(12) United States Patent
Doi et al.

(10) Patent No.: US 9,051,610 B2
(45) Date of Patent: Jun. 9, 2015

(54) RNA IN SITU HYBRIDIZATION

(75) Inventors: Hirofumi Doi, Chiba (JP); Masahiro Matsuoka, Tokyo (JP); Tatsuhiro Nakano, Chiba (JP); Chizuru Nagayoshi, Chiba (JP)

(73) Assignee: CELISH FD, INC., Chiba (JP)

( * ) Notice: Subject to any disclaimer, the term of this patent is extended or adjusted under 35 U.S.C. 154(b) by 349 days.

(21) Appl. No.: 12/993,338

(22) PCT Filed: May 19, 2009

(86) PCT No.: PCT/JP2009/059219
§ 371 (c)(1),
(2), (4) Date: Mar. 23, 2011

(87) PCT Pub. No.: WO2009/142214
PCT Pub. Date: Nov. 26, 2009

(65) Prior Publication Data
US 2011/0183331 A1    Jul. 28, 2011

(30) Foreign Application Priority Data
May 19, 2008 (JP) .................. 2008-131302

(51) Int. Cl.
| C12Q 1/68 | (2006.01) |
|---|---|
| G01N 33/53 | (2006.01) |
| C12M 1/34 | (2006.01) |
| G01N 21/64 | (2006.01) |
| G01N 31/22 | (2006.01) |
| C07H 21/04 | (2006.01) |
| C07H 21/02 | (2006.01) |

(52) U.S. Cl.
CPC ............ *C12Q 1/6832* (2013.01); *C12Q 1/6841* (2013.01)

(58) Field of Classification Search
CPC .. C12Q 1/6841; C12Q 2563/107; C12Q 1/68; C12Q 1/6832; A61K 2039/505
USPC ............... 435/6.1, 6.11, 7.1, 287.2; 536/24.3, 536/25.32; 422/82.07, 430
See application file for complete search history.

(56) References Cited

U.S. PATENT DOCUMENTS

| 5,681,702 A | 10/1997 | Collins et al. | |
|---|---|---|---|
| 2003/0148295 A1* | 8/2003 | Wan et al. ........................ | 435/6 |

FOREIGN PATENT DOCUMENTS

| DK | WO2008068636 | * | 6/2008 |
|---|---|---|---|
| WO | 96/06950 | | 3/1996 |

OTHER PUBLICATIONS

Kazazian et al, The impact of L1 retrotransposons on the human genome, 1998, Nature Genetics, 19, 19-24.*
Wang et al, Survey of plant short tandem DNA repeats, 1994, Theor Appl Genet, 88, 1-6.*
Harper et al, A comparative study of digoxigenin, 2,4-dinitrophenyl, and alkaline phosphatase as deoxyoligonucleotide labels in non-radioisotopic in situ hybridisation, 1997, J Clin Pathol, 50, 686-690.*
Ichinose et al, Detection of cytokine mRNA-expressing cells in peripheral blood of patients with IgA nephropathy using non-radioactive in situ hybridization, 1996, Clin Exp Immunol, 103,125-132.*
Alison et al, Liver Regeneration: A Comparison of in Situ Hybridization for Histone mRNA with Bromodeoxyuridine Labeling for the Detection of S-phase Cells, 1994, The Journal of Histochemistry and Cytochemistry, 42, 1603-1608.*
Zhong et al, The primary structure and expression of four cloned human histone genes,1994, Nucleic Acids Research, 11, 7409-7425.*
Chan et al, e- Sarcoglycan Immunoreactivity and mRNA Expression in Mouse Brain, 2005, The Journal of Comparative Neurology, 482:50-73.*
Olympus BX60 Fluorescence microscope brochure, Down loaded from the internt [www.spachoptics.com], p. 1, printed on Nov. 21, 2012.*
Lunyak et al, Developmentally Regulated Activation of a SINE B2 Repeat as a Domain Boundary in Organogenesis, Science, 2007, 317, 248-251.*
Lunyak et al Supplemental information, Science, 2007, pp. 1-14.*
Scrambled oligo-1 sequence homology with *E. coli* K12 complete genome, Down loaded form the internet [www.ecogne.org/blast], pp. 1-5, printed on Nov. 24, 2012.*
Gonzalez, et al, Small Interfering RNA-mediated Down-regulation of Caveolin-1 Differentially Modulates Signaling Pathways in Endothelial Cells, 2004, The journal of Biochemistry, 279, 40659-40669.*
Chan et al, Method for multiplex cellular detection of mRNAs using quantum dot fluorescent in situ hybridization, 2005, Nucleic Acids Research, 33, e161, pp. 1-8.*
Data sheet, quantum dot molecular weight, down loaded form the internet [www.sigmaaldrich.com], printed on Jun. 24, 2014, p. 1.*
Blast search data sheet DopamineD2 receptor probes 1 and 2 (down loaded from the internet [http://blast.ncbi.nlm.nih.gov]) pp. 1 and 2, printed on Jul. 2, 2014.*
International Search Report issued Jul. 14, 2009 in International (PCT) Application No. PCT/JP2009/059219.
Roche Biochemicals Catalog 2002/2003, 2002, p. 191.

* cited by examiner

*Primary Examiner* — Narayan Bhat
(74) *Attorney, Agent, or Firm* — Wenderoth, Lind & Ponack, L.L.P.

(57) ABSTRACT

A method for identifying the presence of a target gene mRNA is provided, which involves hybridizing one or more oligonucleic acid probes with the target gene mRNA expressed in a tissue sample, and detecting a low-molecular-weight compound label added to at least one of the bases of the oligonucleic acid probes. The oligonucleic acid probes are contacted with the tissue sample for hybridization with the target gene mRNA after pretreating (prehybridizing) one or more dummy oligonucleic acids with the tissue sample, or a mixture of the oligonucleic acid probes and the dummy oligonucleic acids is contacted with the sample tissue to hybridize the oligonucleic acid probes with the target gene mRNA.

10 Claims, 28 Drawing Sheets

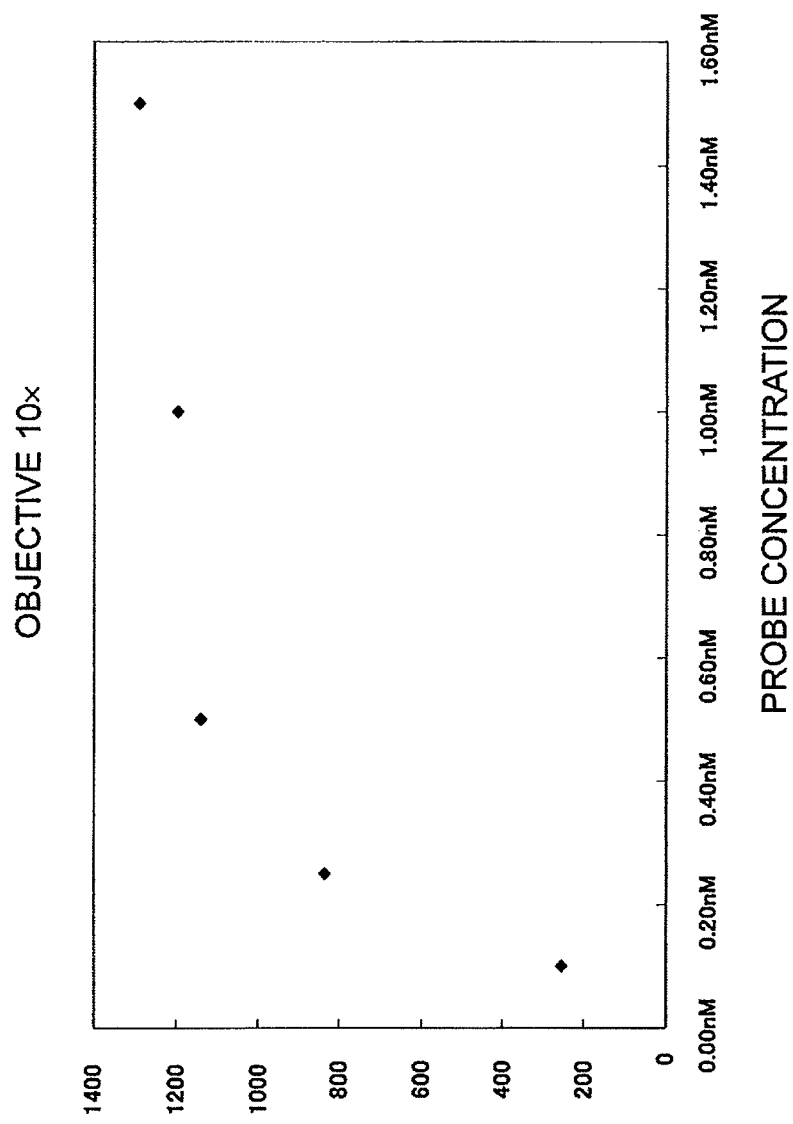

Fig.24
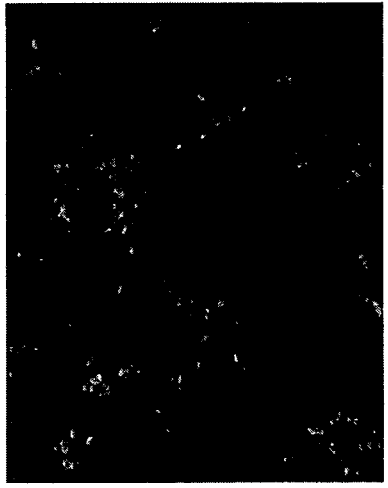
Fig.22b : ActbAS 3' END LABEL PROBE 2
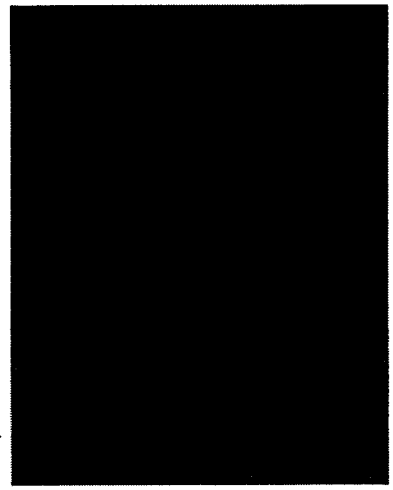
Fig.22d : Actb SENSE PROBE 5', 3' END LABELS
Fig.22a : ActbAS 5' END LABEL PROBE 1
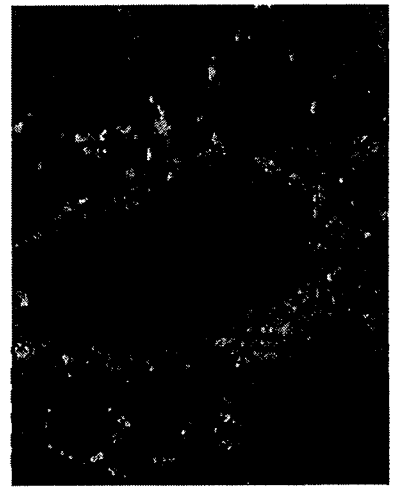
Fig.22c : ActbAS 5', 3' END LABELS Fig.26
PROBE A21 (3' END LABEL) WITH 3' END SEPARATED FROM THE 5' END OF PROBE A1 BY 3 BASES
PROBE A23 (3' END LABEL) WITH 3' END SEPARATED FROM THE 5' END OF PROBE A1 BY 8 BASES
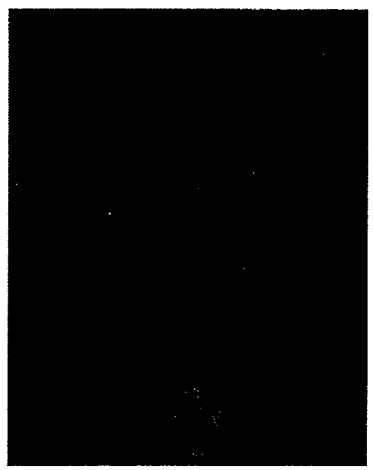
PROBE A22 (3' END LABEL) WITH 3' END SEPARATED FROM THE 5' END OF PROBE A1 BY 5 BASES
PROBE A24 (3' END LABEL) WITH 3' END SEPARATED FROM THE 5' END OF PROBE A1 BY 11 BASES
PROBE A1 LABELED ONLY AT GAPDH 5' END

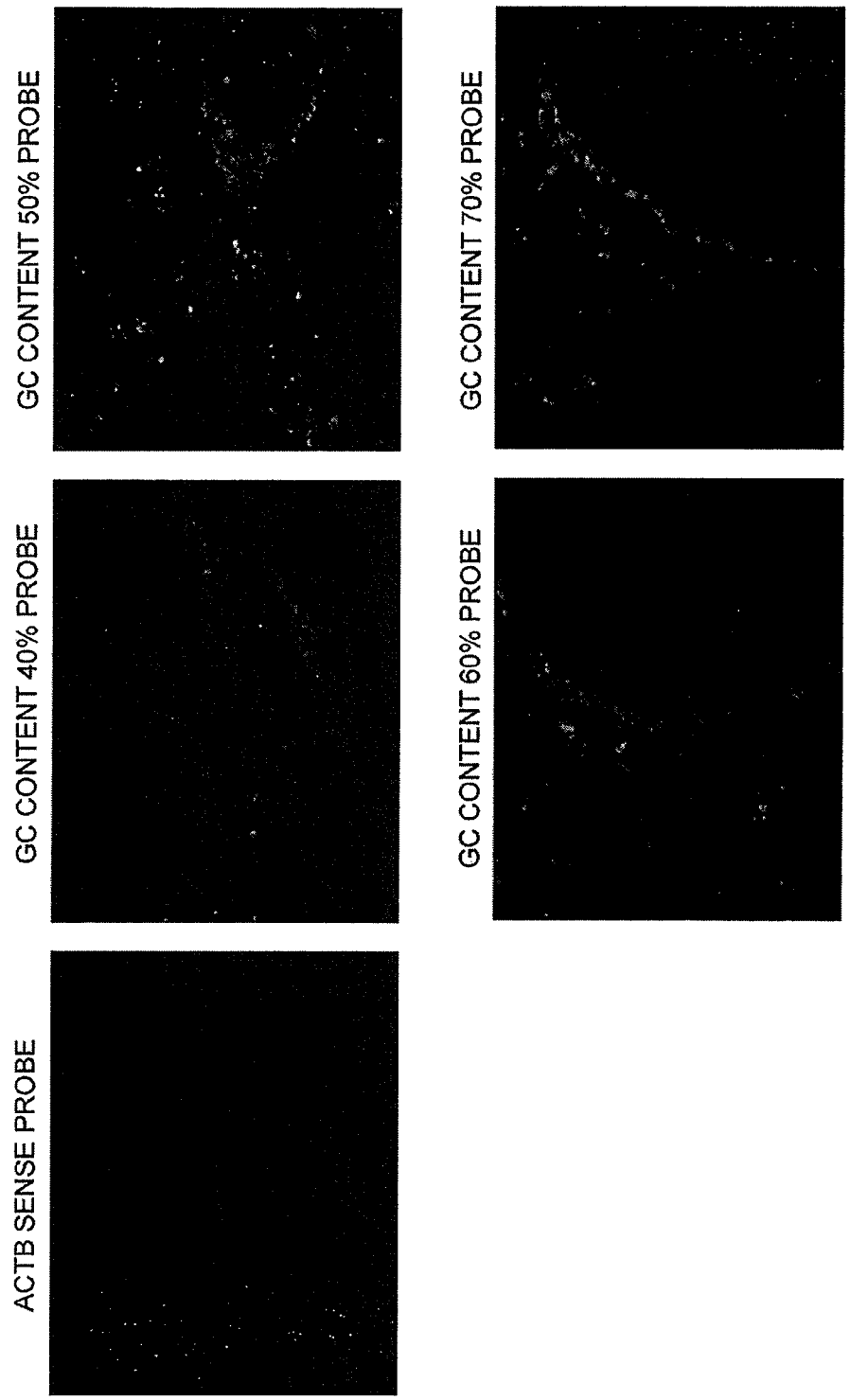

RNA IN SITU HYBRIDIZATION

This application is a U.S. national stage of International Application No. PCT/W2009/059219 filed May 19, 2009.

TECHNICAL FIELD

The present invention relates to RNA in situ hybridization that enables easy pathological and histochemical detection and quantification of gene expression in research and diagnosis.

BACKGROUND ART (1) RNA In Situ Hybridization

Methods of pathological and histochemical detection of gene expression are known. One such method is the in situ hybridization method, in which the messenger RNA (mRNA) as a transcript of gene transcription is detected in situ. The method uses an in situ hybridization buffer in which nucleic acid probes with the nucleic acid sequences complementary to the sequences of the mRNAs to be detected are dissolved (Patent Document 1), and the buffer is added to a tissue sample to hybridize the nucleic acid probes with the mRNAs. Detection labels are added to the nucleic acid probes, and the labels are detected by suitable methods and observed under a microscope (Patent Document 2). In many occasions, digoxigenin (Dig) is used as the label, which is then detected by the anti-digoxigenin antibody portion of an alkaline phosphatase-conjugated anti-digoxigenin antibody protein, and sensitized by alkaline phosphatase-NBT/BCIP chromogenic reaction (Patent Documents 3, 4, 5, and 6). Complementary RNA obtained by the transcription of the full-length or partial sequence of the target mRNA in an in vitro transcription system, or chemically synthesized oligo DNA (Patent Documents 7 and 8), or oligo RNA has been used as the nucleic acid probe.

Close to 40 years have passed since the in situ hybridization method was first published in papers by Pardue and Gall (Non-Patent Document 1) and John et al. (Non-Patent Document 2). Initially, radioactive radioisotopes were used as the labels, and the presence of mRNA was detected upon exposure to a film. This was followed by the development of a non-radioisotopic approach (Patent Document 9), such as the Dig label technique described above (Patent Documents 3, 4, 5, and 6). Aside from the alkaline phosphatase-NBT/BCIP chromogenic reaction for sensitization, tyramide sensitization (TSA sensitization) has been developed to increase detection sensitivity (Patent Documents 10, 11, and 12), and detection techniques using fluorescent dyes also have been developed (Non-Patent Document 3, Patent Documents 13, 14, and 15).

(2) Nucleic Acid Probe

When the nucleic acid probe for the target mRNA is the complementary RNA obtained by transcription in an in vitro transcription system, a Dig label is attached upon incorporation of Dig-UTP by the transcribed complementary RNA in the in vitro transcription system mixed with Dig-UTP (Patent Documents 3, 4, 5, and 6). However, there is no control over the number of Dig-UTPs incorporated into the individual complementary RNA probe molecules, and the locations of the Dig-UTPs on the probe sequences. Further, when complementary RNA is used as the probe, an effort to obtain strong signals has been made through the use of fragmented probes of 300 to 500 bases long prepared by hydrolysis from a long complementary RNA synthesized in an in vitro transcription system. In this case, however, there is no control over the site of hydrolysis, and the probes are obtained as a mixture of various fragments. One way to avoid such a mixture of various fragments is to select one other gene region of about 300 to 500 bases long of high attributes from the full length of the target mRNA using a computer, and to perform RNA in situ hybridization with a complementary RNA probe created in an in vitro transcription system after cloning the selected region. However, the selection of such a region for cloning involves different probe lengths for different genes because of the limitations in the end sequences of the region for the PCR primers, or in the GC content, an important parameter for hybridization. Another drawback is the addition of unnecessary sequences such as a vector used at the 3' end of the complementary RNA, in addition to the selected region, in the in vitro transcription system. As described above, the use of complementary RNA as the probe using an in vitro transcription system involves different probe lengths and uncontrollability in the position and number of the labels added. This is problematic because the probes used for the detection and quantification of the expressed mRNA cannot be quantified. The conventional complementary RNA probes are particularly unsuited for the comparison of the expression levels of different genes, because hybridization conditions are different for the probes used. Further, the use of complementary RNA as a nucleic acid probe involves difficulties in setting experimental conditions. Specifically, because the hybridization process is a type of equilibrium reaction, it requires a search for the probe concentration conditions and hybridization temperature conditions that allow the nucleic acid probes to hybridize with as many mRNA molecules as possible for improved detection sensitivity. Such conditions, however, differ depending on the length and the GC content of the complementary RNA probe used. The process for detecting the hybridized complementary RNA probe also requires a conditional search for antibody concentration, because the antibody reaction for the label detection is also an equilibrium reaction. Further, control of reaction time is required, because the color intensity in the sensitization such as the chromogenic reaction using alkaline phosphatase increases in a manner that depends on reaction time. As described above, the complementary RNA created in an in vitro transcription system for use as a nucleic acid probe is not readily usable because it requires complex processes and conditional searches.

There have been attempts to chemically synthesize oligonucleic acid using a DNA synthesizer or the like for use as a probe. The motivation for this appears to come from the relative ease of creating probes based on the nucleic acid sequences available from database compared with cloning mRNA. Another advantage is the shorter sequences, providing better permeability to tissue samples than that possible with the complementary RNA probes of 300 to 500 bases long. However, this comes with a drawback. Because the oligonucleic acid probe is shorter than the complementary RNA probe, the number of labels per probe is fewer, and accordingly the detected signal intensity of the hybridized oligonucleic acid is weak.

Attempts to overcome this drawback have been made based on two approaches. In the first approach, a fluorescent molecule such as Cy3 and fluorescein is used as the label molecule of the oligonucleic acid probe, and the weak fluorescence that glows from the label fluorescent molecule is captured as a bright spot using a high-magnification objective lens (60× to 100×). The images of large numbers of optical sections along the Z-axis direction are then taken with a CCD camera, and observed after defining the images using a computer algorithm (Patent Document 13). Because the method uses computer processes, the luminance can be measured pixelwise, and the mRNA can be quantified. In this case, attempts to increase signal intensity have been made by providing a distance of at least 10 bases between the label molecules, and thus increasing the number of label molecules added to the probe. As a development of this method, there have been proposed methods for detecting mRNA at the site of transcription using a probe for which a multiplicity of fluorescent molecules with color codes is assigned (Patent Documents 14 and 15).

Another approach includes a technique in which the number of label molecules is increased by adding tails to the outer sides of the probe molecule sequence complementary to the target mRNA, and a method in which signals are sensitized for detection and observation using a sensitization method called TSA (tyramide sensitivity amplification; Patent Documents 10, 11, and 12). The alkaline phosphatase-NBT/BCIP chromogenic sensitization and TSA sensitization have the tendency to increase background noise by the sensitization, and while qualitative microscopy of expression strength has been made, quantification of mRNA levels has not been possible. Further, it has not been possible to compare expression levels between the mRNAs of different genes in the same tissue sample.

[Patent Document 1] U.S. Pat. No. 5,750,340
[Patent Document 2] U.S. Pat. No. 4,888,278
[Patent Document 3] Japanese Patent No. 1,999,884
[Patent Document 4] U.S. Pat. No. 5,344,757
[Patent Document 5] U.S. Pat. No. 5,354,657
[Patent Document 6] U.S. Pat. No. 5,702,888
[Patent Document 7] U.S. Pat. No. 5,597,692
[Patent Document 8] U.S. Pat. No. 6,265,156
[Patent Document 9] U.S. Pat. No. 5,985,549
[Patent Document 10] U.S. Pat. No. 5,196,306
[Patent Document 11] U.S. Pat. No. 5,583,001
[Patent Document 12] U.S. Pat. No. 5,731,158
[Patent Document 13] U.S. Pat. No. 5,866,331
[Patent Document 14] U.S. Pat. No. 6,534,266
[Patent Document 15] JP-T-2002-542793 (the term JP-T as used herein means a published Japanese translation of a PCT patent application)
[Non-Patent Document 1] Pardue M L, and Gall J G. (1969) *Molecular hybridization of radioactive DNA to the DNA of cytological preparations*. Proc Natl Aced Sci USA. 1969 October; 64(2): 600-4
[Non-Patent Document 2] John et al. (1969) *RNA-DNA hybrids at the cytological level*. Nature. 1969 Aug. 9; 223 (5206): 582-7
[Non-Patent Document 3] Levsky J M, and Singer R H, *Fluorescence in situ hybridization: past, present and future*. J. Cell Science, 116, 2833-2838, 2003.

DISCLOSURE OF INVENTION

Problems that the Invention is to Solve

Quantitative PCR methods are used for the quantification of expressed mRNA. However, because the quantitative PCR involves homogenizing the tissue and disrupting the tissue structure, and uses a sample mixture that contains the mRNAs derived from a variety of cells present in the tissue, quantification of the mRNAs expressed in individual cells is not possible. If localization and histochemical quantification of the expressed mRNAs were possible, it would be possible to quantify mRNAs expressed in various cells in the tissue, and provide opportunities for science and industry applications. For example, cancer tissue includes both cancer cells and normal cells, and a variety of cell types exist for the normal cells. Further, many of the cancer tissues include cancer cells with high and low degrees of differentiation. Histochemical detection and quantification of the expressed mRNAs in the cancer cells of such cancer tissues would be highly promising in terms of cancer chemotherapy, if it were usable for the diagnosis of anticancer drug response.

RNA in situ hybridization method is a method for histochemically localizing mRNA in a tissue sample. Conventionally, complementary RNA created in an in vitro transcription system has been commonly used as the probe in the RNA in situ hybridization method. However, the complementary RNA probe is not suitable for quantification, because it does not tell how much mRNA is present, even if pathological and histochemical detection (localization) of the mRNA were possible. Further, while a fluorescent molecule-labeled oligo DNA probe can be used to quantify the expressed mRNA through the measurement of fluorescence intensity using a computer, the detection of fluorescent signals requires a high-magnification objective lens (10× to 60×). Thus, the detectable range of the tissue sample is very narrow, and the mRNA detection involves difficulties in the usual pathological and histochemical methodology in which diagnosis is made over a wide range of a tissue sample using a 10× to 40× objective lens. Further, the detection of mRNA is not easy because the method requires taking images in large numbers of optical sections along the Z-axis direction with the use of an expensive microscope, and defining the images using a special computer algorithm. On the other hand, sensitization methods, such as TSA sensitization, used for the detection of mRNA in a tissue sample using a 10× to 40× objective lens simultaneously amplify not only target signals but background noise. Accordingly signal-noise ratio (SN ratio) is poor, and quantification of mRNA is difficult.

Generally, fish (typically, salmon) sperm DNA or yeast tRNA is used to lower background noise in RNA in situ hybridization. The tissue sample, being a biological sample, includes large numbers of sites for the non-specific adsorption of nucleic acid probes molecularly equivalent to biomacromolecules. The nucleic acid probes non-specifically adsorbed to the tissue sample cause background noise. This is particularly problematic when signals are sensitized using a sensitization method, as it simultaneously amplifies background noise and degrades SN ratio. The background noise can be lowered by preventing the non-specific adsorption of the nucleic acid probes to the tissue sample. This can be realized by using single-stranded fish sperm DNA or yeast tRNA fragmented into about 2,000 bases long by sonication, and by prehybridizing the fragments to the non-specific adsorption sites prior to nucleic acid probe hybridization. Alternatively, the fish sperm DNA or yeast tRNA is used as a mixture with the nucleic acid probes in a hybridization solution.

However, when used with oligonucleic acid probes, there is a possibility that the single-stranded fragments of fish sperm DNA of about 2,000 bases may present hybridization sites for the oligonucleic acid probes. These sites may compete with the target mRNA in the tissue sample intended for hybridization, preventing hybridization of the oligonucleic acid probes with the target mRNA, and possibly lowering the intended signals. In other cases, the oligonucleic acid probes hybridized with the fish sperm DNA cause background noise, which is amplified by sensitization. Further, despite that the fish sperm DNA is fragmented into about 2,000 bases long, the oligonucleic acid probes are still shorter than the fish sperm DNA, and are therefore highly permeable to the tissue sample. Accordingly, the tissue sample may present non-specific adsorption sites inaccessible to the fish sperm DNA. This may also lead to increased background noise.

The present invention has been made in view of the foregoing problems, and an object of the invention is to realize accurate and easy detection of mRNA expression level-dependent changes in signal intensity with the use of a 10× to 40× objective lens after signal amplification with reduced background noise, and to thereby provide means by which pathological and histochemical detection and quantification of expressed mRNA can be realized and used for research and diagnostic purposes.

Means for Solving the Problems

The present inventors used a dummy oligonucleic acid of substantially the same length as the length of an oligonucleic acid probe for the purpose of preventing non-specific adsorption of the oligonucleic acid probe to the tissue sample, instead of using the sperm DNA of fish such as salmon commonly used in RNA in situ hybridization, and found that this improves the SN ratio and enhances signals in images taken by simple means of a CCD camera with a fluorescence microscope equipped with a 10× to 20× objective lens according to a sensitization method. It was also found that, with the use of the dummy oligonucleic acid, the observed signal intensity additively increases with increase in the number of oligonucleic acid probe labels. The observed signal intensity was also found to additively increase as the number of oligonucleic acid probe sequences with the same number of labels is increased in the detection of the expressed mRNA of a single gene. Another finding is that the observed signal intensity increases as an increasing function of the GC content in the oligonucleic acid probe sequence. It was also found that the observed signal intensity increases as an increasing function of the probe Tm value.

The present invention provides the followings based on the foregoing novel findings by the present inventors.

(1) An RNA in situ hybridization method for identifying the presence of mRNA of a target gene, which comprises hybridizing one or more oligonucleic acid probes with mRNA of the target gene expressed in a tissue sample, and detecting a low-molecular-weight compound label added to at least one of the bases of the oligonucleic acid probes, wherein the oligonucleic acid probes are contacted with the tissue sample for hybridization with mRNA of the target gene after pretreating (prehybridizing) one or more different dummy oligonucleic acids with the tissue sample, or a mixture of the oligonucleic acid probes and the dummy oligonucleic acids is contacted with the sample tissue to hybridize the oligonucleic acid probes with mRNA of the target gene, and wherein the dummy oligonucleic acids are substantially equal in length with the oligonucleic acid probes, and are neither hybridizable with regions of the target gene mRNA with which the oligonucleic acid probes hybridize nor with the oligonucleic acid probes.

(2) The RNA in situ hybridization method of (1), wherein the amounts of the dummy oligonucleic acids are 2 to 10 times the amounts of the oligonucleic acid probes.

(3) The RNA in situ hybridization method of (2), wherein the oligonucleic acid probes and the dummy oligonucleic acids are substantially equal in base length within a range of from 20 bp to 70 bp.

(4) The RNA in situ hybridization method of (1), wherein the low-molecular-weight compound label is added to a 5' end base and/or a 3' end base of the oligonucleic acid probes, (5) The RNA in situ hybridization method of (1), wherein two or more of the oligonucleic acid probes of (4) are hybridized with the mRNA by being separated from each other by a distance of 8 or more bases between the 5' end of one probe and the 3' end of the other probe.

(6) The RNA in situ hybridization method of (1), further including:

sensitizing a detection signal using an antibody for the low-molecular compound, an enzyme conjugated with the antibody, and a color-developing compound or a fluorescent molecule compound used as a substrate for the enzyme; and detecting the signal with a 10× to 40× objective lens.

(7) The RNA in situ hybridization method of (1), wherein the tissue sample is a tissue isolated from mammal, and wherein the dummy oligonucleic acids are oligonucleic acids that correspond to partial sequences of retrotransposon repeat sequences.

(8) The RNA in situ hybridization method of (1), wherein the tissue sample is a tissue isolated from mammal, and wherein the dummy oligonucleic acids are oligonucleic acids that correspond to part of a plant genome, or partial sequences of a microorganism genome.

(9) The RNA in situ hybridization method of (1), wherein the dummy oligonucleic acids are oligonucleic acids obtained by the A-to-T, T-to-A, G-to-C, and C-to-G substitutions of the base sequences of the oligonucleic acid probes, the dummy oligonucleic acids including the substitution of M×0.2 bases (rounded up to the nearest integer) to M×0.8 bases (rounded down to the nearest integer) with the complementary bases in a contiguous sequence of M or more same bases (M=4) when M or more same bases are present, and the dummy oligonucleic acids including the substitution of at least N×0.2 bases (rounded up to the nearest integer) with the complementary bases in the presence of a palindromic sequence of N or more bases (N=5) identical to its complementary sequence when read from the 5' side or 3' side, the at least N×0.2 bases being at most (N/2−1) bases when N is an even number, and being at most ((N−1)/2−1) bases when N is an odd number.

(10) A set of dummy oligonucleic acids used for the RNA in situ hybridization method of (7), wherein the dummy oligonucleic acids are partial sequences of retrotransposon repeat sequences, or different partial sequences of the repeat sequences.

(11) A set of dummy oligonucleic acids for the RNA in situ hybridization method of (8), wherein the dummy oligonucleic acids are part of a plant genome or partial sequences of a microorganism genome, or different partial sequences of a plant genome or a microorganism genome.

The present invention enables pathological and histochemical detection and quantification of expressed mRNA both easily and accurately, and thus drives the development of basic research directed to, for example, finding the cause and treatment of various diseases. The invention therefore has large contributions to improving the diagnosis accuracy of various diseases.

BRIEF DESCRIPTION OF DRAWINGS

FIG. 14a represents the correlation between signal intensity and probe concentration in Example 6.

FIG. 24 represents the signal intensity of in situ hybridization for the rat actin beta gene Actb in rat lungs, confirming the effects of the position (5' end or 3' end) and the number of oligonucleic acid probe labels in Example 12.

FIG. 26 represents the result of RNA in situ hybridization performed to confirm the required distance between two labels on an mRNA nucleic acid sequence in the detection of a hybridized product using more than one label on a single-gene mRNA in Example 13.

FIG. 27 represents the results of in situ hybridizations performed with oligonucleic acid probes of varying GC contents in Example 14.

BEST MODE FOR CARRYING OUT THE INVENTION

Figure 1:
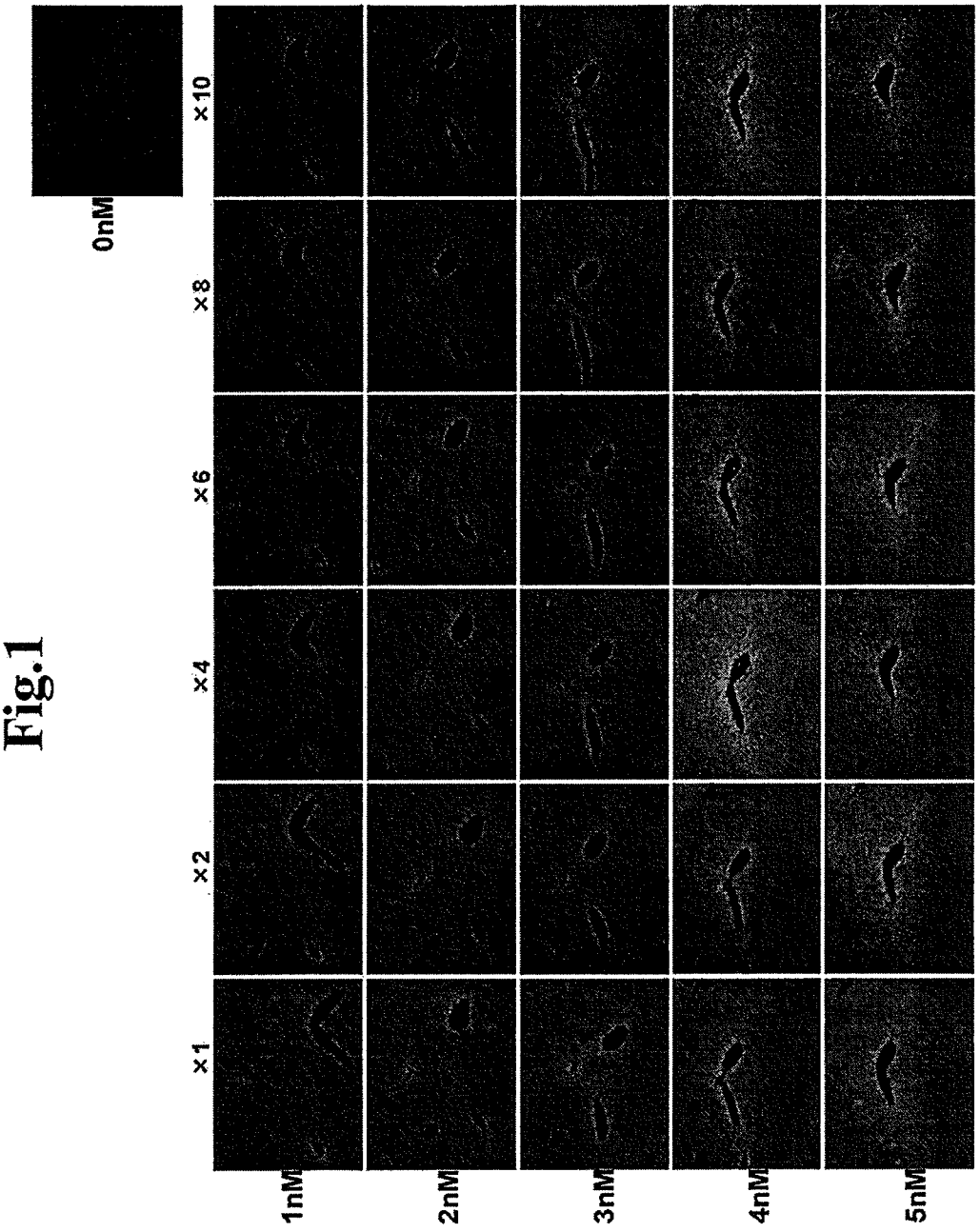
FIG. 1 represents the result of RNA in situ hybridization performed to determine the optimum addition ratio of dummy oligo DNA for the concentration of oligo DNA probes in Example 1.

Invention (1) is characterized by the use of one or more dummy oligonucleic acids that neither hybridize with a target gene mRNA in regions hybridized with oligonucleic acid probes nor with the oligonucleic acid probes. Specifically, single-stranded oligonucleic acid probes are contacted with a tissue sample for hybridization with the target gene mRNA after the tissue sample is pretreated (prehybridized) with single-stranded dummy oligonucleic acids, or a mixture of the single-stranded oligonucleic acid probes and the single-stranded dummy oligonucleic acids is contacted with the tissue sample to hybridize the single-stranded oligonucleic acid probes with the target gene mRNA. The target genes are about 1 to 10 gene mRNAs expressed in the tissue sample.

The dummy oligonucleic acids can be chemically synthesized under the condition that the dummy oligonucleic acids neither hybridize with regions of the target gene mRNA with which the oligonucleic acid probes hybridize nor with the oligonucleic acid probes. Commercially available automated DNA synthesizers can be used for the chemical synthesis, or the dummy oligonucleic acids may be synthesized using DNA synthesis services. The condition that the dummy oligonucleic acids do not hybridize with the target gene mRNA in regions hybridized with the oligonucleic acid probes has the same meaning as having a different base sequence as the oligonucleic acid probe that hybridizes with the target gene mRNA. A different base sequence may be measured with reference to a percentage match of 30% or less, preferably 20% or less, further preferably 10% or less in a base sequence comparison using, for example, BLAST. Alternatively, the measure of a different base sequence may be a difference in a contiguous base sequence that corresponds to at least 70%, preferably at least 80%, further preferably at least 90% of the full length of the oligonucleic acid probe. The condition that the dummy oligonucleic acids do not hybridize with the oligonucleic acid probes may be measured with reference to a percentage match of 30% or less, preferably 20% or less, further preferably 10% or less in a base sequence comparison with the complementary sequence of the oligonucleic acid probe using, for example, BLAST. Alternatively, the measure of difference may be a difference in a contiguous base sequence that corresponds to at least 70%, preferably at least 80%, further preferably at least 90% of the full length of the complementary sequence of the oligonucleic acid probe.

One or more (2 to 5) kinds of dummy oligonucieic acids may be used. Two of the different kinds of dummy oligonucleic acids may have complementary sequences to each other.

The amount of dummy oligonucleic acid, specifically, the concentration of the dummy oligonucleic acid in a prehybridization solution or a hybridization solution (described later) may be 2 to 10 times, preferably 6 to 8 times higher than the amount of oligonucleic acid probe, specifically, the concentration of the oligonucleic acid probe in the hybridization solution. When more than one oligonucleic acid probe is used, the total concentration value becomes the oligonucleic acid probe amount. Similarly, when more than one dummy oligonucleic acid is used, the total concentration value becomes the dummy oligonucleic acid amount.

The dummy oligonucleic acid has substantially the same length as the oligonucleic acid probe. As used herein, "substantially the same length" means a difference of ±10%, preferably ±5%, further preferably ±3%, particularly preferably ±0% (completely the same). The oligonucleic acid probe may be 20 bp to 70 bp long. Accordingly, the dummy oligonucleic acid, having substantially the same length as the oligonucleic acid probe, has this range of base length.

A nucleic acid sequence that does not hybridize with the target gene mRNA, but hybridizes with the mRNAs of other genes may be selected as the dummy oligonucleic acid. Further, a sequence of substantially the same length as the oligonucleic acid probe may be selected from the retrotransposon-derived repeat sequences that recurrently occur in mammal genomes. Further, a sequence of substantially the same length may be selected from the gene sequences of plants or microorganisms not present in mammals.

For the selection of dummy oligonucleic acids, a simple computer program can be used to calculate the GC content in a partial sequence of a desired length created by the base-by-base 5' base shifting of the genome repeat sequence or the plant or microorganism gene sequence used for the dummy oligonucleic acid selection. A listing of oligonucleic acid sequences with desired GC contents can then be made. The oligo sequences in the listing are then run through a BLAST search to ascertain the degree of match with the oligonucleic acid probes, and those having a poor match with the oligonucleic acid probes are selected. Because the BLAST search is simultaneously run for the complementary strands, those having a poor match with the complementary strands of the oligonucleic acid probes are simultaneously selected.

Further, the dummy oligonucleic acid may be, for example, an oligonucleic acid obtained by the sequential A-to-T, T-to-A, G-to-C, and C-to-G substitutions of the oligonucleic acid probe base sequence from the 5' side. In the presence of a contiguous sequence of M or more same bases (M=4), the dummy oligonucleic acid also includes the substitution of M×0.2 (rounded up to the nearest integer) to M×0.8 (rounded down to the nearest integer) bases in the contiguous sequence with the complementary bases. In the presence of a palindromic sequence (the same whether read from the 5' side or the 3' side) with N bases (N=5) or more, the dummy oligonucleic acid also includes the substitution of at least N×0.2 (rounded up to the nearest integer) bases [at most (N/2−1) when N is an even number, and at most ((N−1)/2−1) bases when N is an odd number] with the complementary bases. In either case, the dummy oligonucleic acid has the same GC content and the same length as the oligonucleic acid probe.

The oligonucleic acid probe has a low-molecular-weight compound label added to at least one of the bases. Two or more kinds of low-molecular-weight compound labels may be added. For example, digoxigenin (Dig), or fluorescent dyes such as FITC (fluorescein isothiocyanate; Non-Patent Document 3) used in conventional methods may be used as the low-molecular-weight compound label. When Dig is used for example, an alkaline phosphatase-linked anti-digoxigenin antibody protein is used to detect the Dig label at the anti-digoxigenin antibody portion, and a chromogenic reaction is induced by alkaline phosphatase-NBT/BCIP for sensitization (Patent Documents 3, 4, 5, and 6). Aside from the alkaline phosphatase-NBT/BCIP-induced chromogenic reaction, sensitization methods such as tyramide sensitization (TSA sensitization) that involves the reaction of tyramide-fluorescent dye molecules with a peroxidase-conjugated anti-digoxigenin antibody protein or a peroxidase-conjugated anti-FITC antibody protein may be used (Patent Documents 10, 11, and 12).

In a preferred embodiment, the addition of the low-molecular-weight compound label is made at the 5' end base and the 3' end base of the oligonucleic acid probe. Synthesis of such labeled oligonucleic acids can easily be made using oligo DNA synthesis services.

One or more oligonucleic acid probes, specifically 1 to 20, preferably 1 to 10, more preferably 1 to 5 oligonucleic acid probes are hybridized with different regions of a single target gene mRNA. Hybridization time can be reduced with the use of more than one oligonucleic acid probe. The concentration range of the oligonucleic acid probe may be from 0.01 nM to 10 nM. Hybridization time also can be reduced particularly by increasing the concentration within this range. When using more than one oligonucleic acid probe, it is preferable that the oligonucleic acid probes have substantially the same GC content. As used herein, substantially the same GC content means a difference of ±10%, preferably ±5%, further preferably ±3%, particularly preferably ±0% (completely the same).

Note that when more than one oligonucleic acid probe having a label at the both ends is hybridized with the target gene mRNA, the 5' end and the 3' end of the probes are separated from each other by at least 8 bases. In a preferred embodiment, the 5' end and the 3' end of the probes are separated from each other by the distance equal to or greater than the lengths of the oligonucleic acid probes used.

More than one oligonucleic acid probe for the target gene mRNA can be designed as follows. First, using a simple computer program, GC content calculations are performed in a window of a desired oligonucleic acid probe length while shifting the window base by base from the 5' end to the 3' end of the target gene mRNA. As a result, a listing of candidate probe sequences with the desired GC contents is easily created. Then, the specificity of the listed candidate sequences as the probe sequences is ascertained using the BLAST search available from NCBI (National Center for Biotechnology Information, U.S.A.). The complementary strands of the sequences with high specificity can then be easily selected as the oligonucleic acid probe sequences.

Basically, the solutions described in Patent Document 1 can be used as the buffer for the hybridization (hybridization solution). In the present invention, 12.5% to 25% formamide, 3×SSPE (Invitrogen), 1×Denhardt (Wako Pure Chemical Industries, Ltd.), 10% dextran (V/V; Sigma), and 0.2% CHAPS (Sigma-Aldrich) were used in the final solution. Generally, yeast or *Escherichia coli* tRNA is added thereto. The hybridization temperature, which depends on the length and GC content of the oligo DNA probe used, ranges from 30° C. to 45° C. For example, when the oligo DNA probe is 40 bases long and has the GC content of 50%, hybridization is preferably performed at a temperature of from 40° C. to 42° C. Hybridization time is 12 hours to 24 hours, preferably 16 hours.

Quantitative detection of the target gene mRNA is possible based on the foregoing RNA in situ hybridization method. For example, when a digoxigenin (Dig) label is used, TSA sensitization using a tyramide-fluorescent dye is performed with a peroxidase (POD)-conjugated anti-digoxigenin antibody. The tissue sample is then taken with a CCD camera through a fluorescence microscope equipped with a 10× to 40× objective lens. The resulting micrographs are then computer processed using image processing software such as Image J (NIH, http://rsb.info.nih.gov/ij/) to determine the signal intensity of the fluorescent dye. Quantitative detection of the expression level of the target gene mRNA can easily be performed in this manner.

Reagents and tyramide-fluorescent molecules for tyramide sensitization are commercially available from Perkin Elmer and Invitrogen, and these can be used herein. Antibodies for the POD-conjugated label molecules are commercially available from Dako and Roche, and these can be used herein.

When oligonucleic acid probes including two or more labels i added as the low-molecular-weight compound labels are used, sensitization is performed stepwise by tyramide sensitivity amplification using a tyramide-fluorescent dye i, with the use of antibodies for the POD-conjugated labels i, followed by multiple detection of fluorescent dye i signals using a fluorescence microscope. In this way, localization and quantification of the mRNAs of two or more target genes are possible. When the expression levels of the target genes are low, the detection range can be widened by increasing the number of oligonucleic acid probes that hybridize with the target gene mRNAs, or by increasing the concentration of the oligonucleic acid probes. Conversely, when the expression levels of the target genes are high, the detection range can be narrowed down to the level of the gene mRNAs of low expression levels by decreasing the number of labels for the oligonucleic acid probes that hybridize with the target gene mRNA, or by decreasing the number or concentration of the oligonucleic acid probes, or the concentration of the tyramide-fluorescent dye used. In this way, the mRNA of more than one gene with different expression levels can be localized and quantified at the same levels of signal intensity and range, and used for pathological tissue diagnosis or other applications, The following specifically describes the present invention in more detail based on Examples. The present invention, however, is not limited to the descriptions of the following Examples.

In the Examples, synthetic oligonucleic acids of the following base sequences were used.

```
SEQ ID NO: 1:
5'-catccagaacactaaacagaagatggcagtggccagtagc-3'

SEQ ID NO: 2:
5'-gaagaagtccactgcattccctgaggtgacattctccaca-3'
```

-continued
```
SEQ ID NO: 3:
5'-tcattgaaggtcttaaacctcttgagggccgggttgggca-3'

SEQ ID NO: 4:
5'-cgctgtgcttgaacagggcacttgtgatgtcttggatact-3'

SEQ ID NO: 5:
5'-tagtcccagctactcaggaagctgaggtgggaggatggct-3'

SEQ ID NO: 6:
5'-gctcccggcgatacgagggtccgatcttagctcgttgaca-3'

SEQ ID NO: 7:
5'-cttataagtgggagctgaacaatgagaacacatggacaca-3'

SEQ ID NO: 8:
5'-gggaggggaacattgcacaccagggcctgttgtgggggag-3'

SEQ ID NO: 9:
5'-agccatcctcccacctcagcttcctgagtagctgggacta-3'

SEQ ID NO: 10:
5'-tgtgtccatgtgttctcattgttcagctcccacttataag-3'

SEQ ID NO: 11:
5'-ctcccccacaacaggccctggtgtgcaatgttcccctccc-3'

SEQ ID NO: 12:
5'-ctggagatactgggaaaaggcaatcaggactaggcctttg-3'

SEQ ID NO: 13:
5'-cgcagtgtccgaggaagatagctgttccttaactttggca-3'

SEQ ID NO: 14:
5'-caggggttatatccgttttaaccggaagtccagtattggc-3'

SEQ ID NO: 15:
5'-gaacagctatattcctcggacactgcg-3'

SEQ ID NO: 16:
5'-ggtagaggcgaagtccttatcttccac-3'

SEQ ID NO: 17:
5'-attgatgccaagactggacttccggtta-3'

SEQ ID NO: 18:
5'-tgtccttccaaatgagctggcaagtg-3'

SEQ ID NO: 19:
5'-ggagtttcccaaacactcagtgaaacaaag-3'

SEQ ID NO: 20:
5'-acttcaacaagaacagtatccaagacatcac-3'

SEQ ID NO: 21:
5'-gggtgcatcgctggtaacatcc-3'

SEQ ID NO: 22:
5'-ctcaagatcgcattcatgcgtcttcac-3'

SEQ ID NO: 23:
5'-aaatcccttcacactcttttggagata-3'

SEQ ID NO: 24:
5'-aagcacatggcaccaatgacgttagccaccgattccacca-3'

SEQ ID NO: 25:
5'-gtcttggtagtgctcctggacagttttctgcagaaacagc-3'

SEQ ID NO: 26:
5'-atgttgacaatcttctcctcggggatgagaccgccattgt-3'

SEQ ID NO: 27:
5'-ctcatggatcttcctctgcacgttaggccatgtcacaagt-3'

SEQ ID NO: 28:
5'-cggcaacacacgtctttgcaaagtctgttacttcctgcac-3'

SEQ ID NO: 29:
5'-ctttaatgtcacgcacgatttccctctcagctgtggtggt-3'
```

-continued

SEQ ID NO: 30:
5'-atttctcgtggttcacacccatcacaaacatgggggcatc-3'

SEQ ID NO: 31:
5'-gtggtgcaggatgcattgctgacaatcttgagggagttgt-3'

SEQ ID NO: 32:
5'-tggtggtgcaggatgcattgctgacaatcttgagggagtt-3'

SEQ ID NO: 33:
5'-agttggtggtgcaggatgcattgctgacaatcttgaggga-3'

SEQ ID NO: 34:
5'-agcagttggtggtgcaggatgcattgctgacaatcttgag-3'

SEQ ID NO: 35:
5'-aattgaatgtagtttcatggatgccacaggattccatacc-3'

SEQ ID NO: 36:
5'-ggatgcggcagtggccatctcttgctcgaagtctagggca-3'

SEQ ID NO: 37:
5'-ctgtcaggtcccggccagccaggtccagacgcaggatggc-3'

SEQ ID NO: 38:
5'-cagaaccatcacgaggacctgtcataagacgtctttgtcg-3'

SEQ ID NOS: 1 to 4 represent oligonucleic acid base sequences that hybridize with mouse Cyp1a2 gene mRNA.

SEQ ID NOS: 5, 7, and 8 represent oligonucleic acid base sequences that comprise the partial sequences of human transposon repeat sequences. SEQ ID NOS: 9-11 represent oligonucleic acid base sequences that comprise the complementary sequences of SEQ ID NOS: 5, 7, and 8.

SEQ ID NO: 6 represents an oligonucleic acid base sequence that comprises a partial sequence of an *Arabidopsis thaliana* POD gene.

SEQ ID NO; 12 represents an oligonucleic acid base sequence that hybridizes with mouse alb gene mRNA. SEQ ID NOS: 13 and 14 represent oligonucleic acid base sequences that hybridize with mouse Arntl gene mRNA.

SEQ ID NOS: 15 and 16 represent the base sequences of a PCR primer set for a mouse Arntl gene. SEQ ID NO: 17 represents the base sequence of a TaqMan Probe for a mouse Arntl gene.

SEQ ID NOS: 18 and 19 represent the base sequences of a primer set for a mouse Cyp1a2 gene. SEQ ID NO: 20 represents the base sequence of a TaqMan Probe for a mouse Cyp1a2 gene.

SEQ ID NOS: 21 and 22 represent the base sequences of a primer set for a mouse Alb gene. SEQ ID NO: 23 represents the base sequence of a TaqMan Probe for a mouse Alb gene.

SEQ ID NOS: 24-27 represent oligonucleic acid base sequences that hybridize with mouse Cyp1a2 gene mRNA.

SEQ ID NO: 28 represents an oligonucleic acid base sequence that hybridizes with mouse Alb gene mRNA.

SEQ ID NO: 29 represents an oligonucleic acid base sequence that hybridizes with rat Actb gene mRNA. SEQ ID NOS: 30-34 represent oligonucleic acid base sequences that hybridize with rat Gapdh gene mRNA. SEQ ID NOS: 35-37 represent oligonucleic acid base sequences that hybridize with rat Actb gene mRNA.

SEQ ID NO: 38 represents an oligonucleic acid base sequence synthesized by the sequential A-to-T, T-to-A, G-to-C, and C-to-G substitutions of the oligonucleic acid of SEQ ID NO: 27 from the 5' side, and by the substitution of the TTTT contiguous sequence with ATAA.

EXAMPLE 1

Experiment on Addition Ratio of Dummy Oligonucleic Acid

Figure 2:
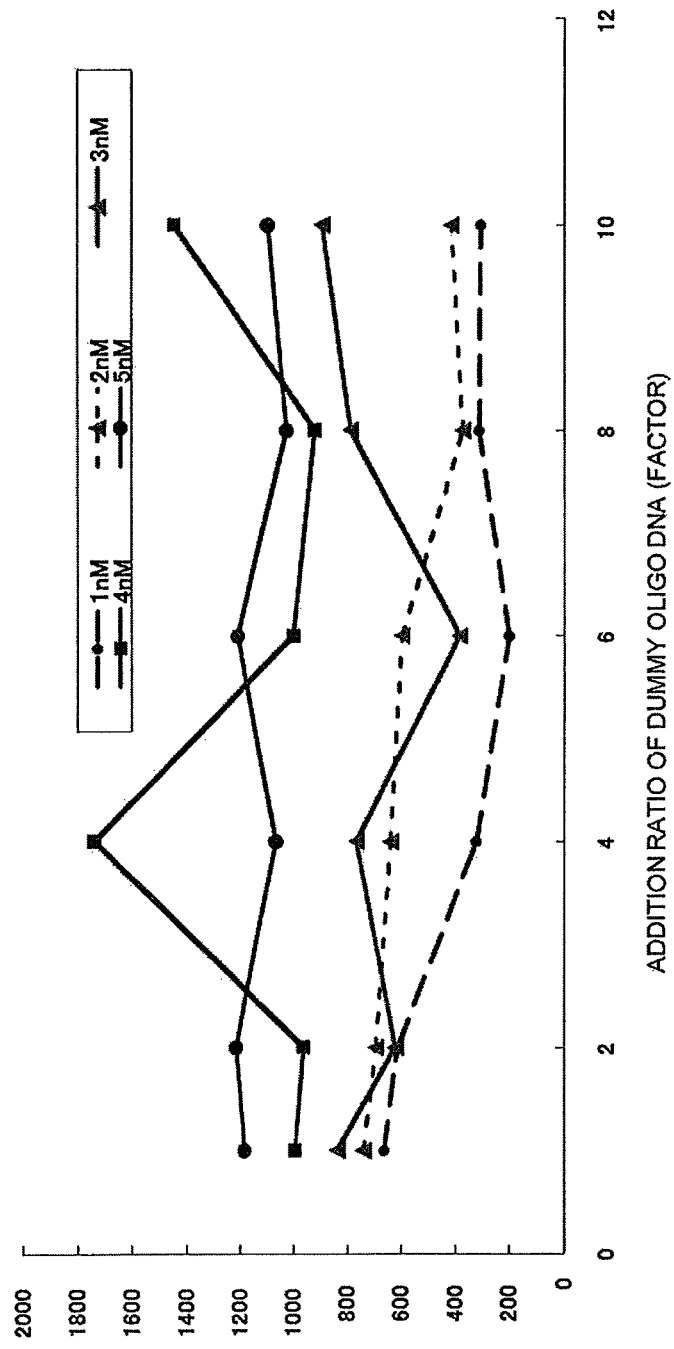
FIG. 2 represents the signal intensity determined for each addition ratio from the result of RNA in situ hybridization in Example 1, determining the optimum addition ratio of dummy oligo DNA for the concentration of oligo DNA probes.
Figure 3:
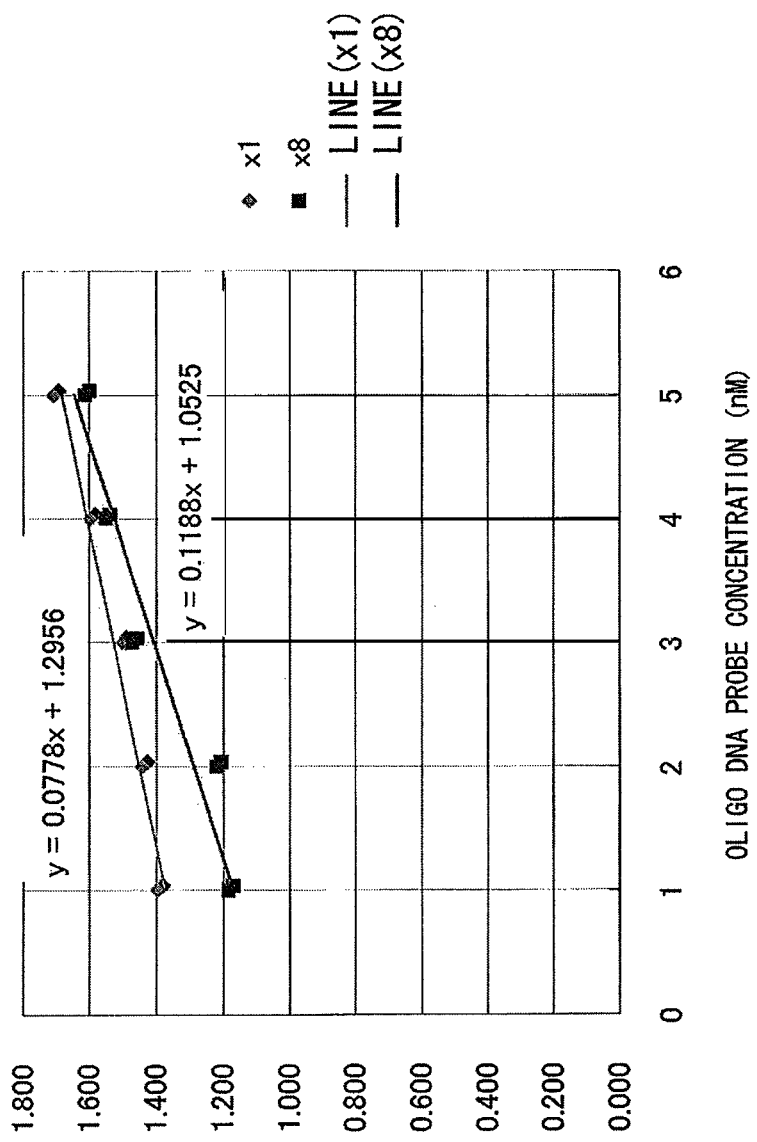
FIG. 3 represents the signal intensity determined at each probe concentration for the addition ratios of 1 and 8 in Example 1, determining the optimum addition ratio of dummy oligo DNA for the concentration of oligo DNA probes.

The optimum addition ratio of dummy oligo DNA for probe concentration was determined. Mouse liver was used as the subject tissue, and the gene Cyp1a2 was used as the detection target. The liver of a male mouse, 8 weeks of age, was prepared into a paraffin block using the usual formalin fixation and paraffin embedding, and 5-micron thick serial sections were made. Following deparaffinization, the specimens were treated with Protease K (Invitrogen, Proteinase K SOL. RNA, 25530049), and RNA in situ hybridization was performed. Four single-stranded oligo DNA probes (SEQ ID NOS: 1 to 4) FITC-labeled at the both ends were used as the probes for detecting Cyp1a2 gene mRNA. SEQ ID NOS: 1 to 4 are aligned in this order from the 5' end to the 3' end on the Cyp1a2 gene mRNA. The adjacent oligo DNA probes are separated from each other by a distance of 594 bases between SEQ ID NOS: 1 and 2, 16 bases between SEQ ID NOS: 2 and 3, and 61 bases between SEQ ID NOS: 3 and 4. A dummy oligo DNA (single-stranded) represented by SEQ ID NO: 5 was used. For the detection of the FITC labels, the anti-FITC rabbit polyclonal antibody P5100 (Dako) was used, and TSA sensitization was performed using a tyramide-FLU (Perkin-Elmer, TSA Plus Fluorescein System, NEL741B001KT). FIG. 1 represents the results of quantitative RNA in situ hybridization performed with hybridization solutions that contained the dummy oligo DNA at 1×, 2×, 4×, 6×, 8×, and 10× concentrations with respect to each different concentration 1 nM (nanomol), 2 nM, 3 nM, 4 nM, and 5 nM of the four probes, specifically, each total concentration of 4 nM, 8 nM, 12 nM, 16 nM, and 20 nM. As a control, 200 nM dummy oligo DNA was added for a probe concentration of 0 nM. Images were taken in the same regions of the serial sections with a 10× objective lens, using a Zeiss fluorescence microscope Axioplan2 and a CCD camera AxioCam. The image data were computer processed using Image J software (NIH, http://rsb.info.nih.gov/ij/), and the value obtained by subtracting the signal intensity at 0 nM probe concentration from the signal intensity in each image was determined as the signal intensity of each image. FIG. 2 represents the relationship between the addition ratio of the dummy oligo DNA and the resulting signal intensity obtained by the detection of the Cyp1a2 gene mRNA. The horizontal axis represents the addition ratio of the dummy oligo DNA, and the vertical axis represents signal intensity (IntDen). As can be seen in FIG. 2, an orderly relationship is maintained between oligo DNA probe concentration and signal intensity at the dummy oligo DNA addition ratio of 8, and the signal intensity at this ratio has a wider range than at the ratio 1 at which the orderly relationship is also maintained. It can also be seen from FIG. 2 that the signal intensity generally increases with increase in probe concentration. Further, the factor by which the fluorescence intensity surpasses the fluorescence intensity of the image at the oligo DNA probe concentration of 0 nM was calculated as the ratio of fluorescence intensities (FIG. 3), based on images at the addition ratios of 8 and 1 at which an orderly relationship is maintained between oligo DNA probe concentration and signal intensity. The ratio indicates an increase in background noise when the RNA in situ hybridization signal is weak at low probe concentrations as in, for example, 1 nM. Specifically, it can be seen from FIG. 3 that the ratio is greater and the background noise is higher at the dummy oligo DNA addition ratio of 1 than at 8. On the other hand, at high oligo DNA probe concentrations, the ratio indicates an increase in the signal intensity of RNA in situ hybridization. The signal intensity of the image as a whole becomes lower at the addition ratio of 8, because of the lower background noise than at the addition ratio of 1. However, the rate of ratio increase is higher at the addition ratio of 8 than 1 as the oligo DNA probe concentration increases, showing that the dynamic range is wider for the addition ratio of 8. It can be seen from FIG. 3 that the dynamic range is 1.375 times greater at the addition ratio of 8 than 1.

EXAMPLE 2

Comparison Between Dummy Oligo DNA, Salmon Sperm DNA, and No Addition

Figure 4:
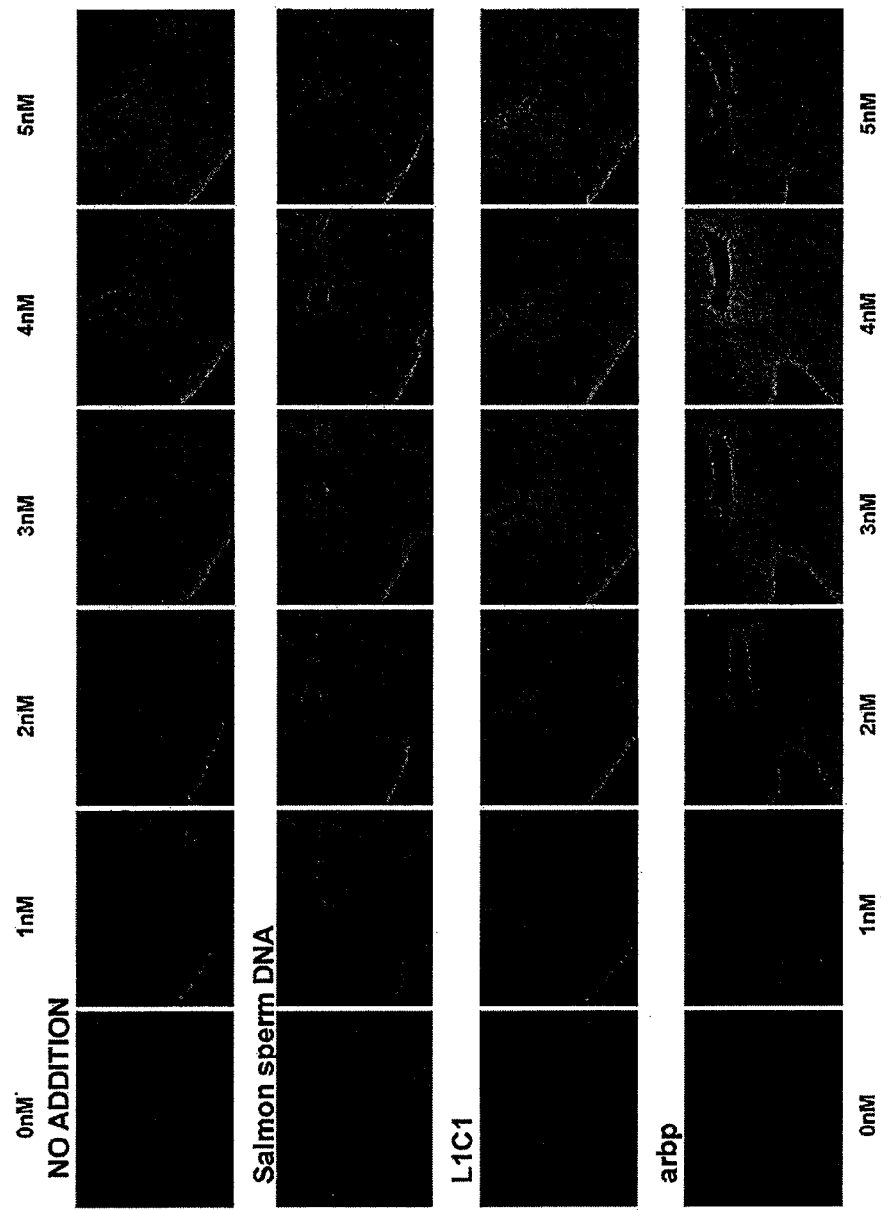
FIG. 4 represents the result of RNA in situ hybridization performed to determine the effects of adding two dummy oligo DNAs, salmon sperm DNA, and no components at each oligo DNA probe concentration in Example 2.
Figure 5:
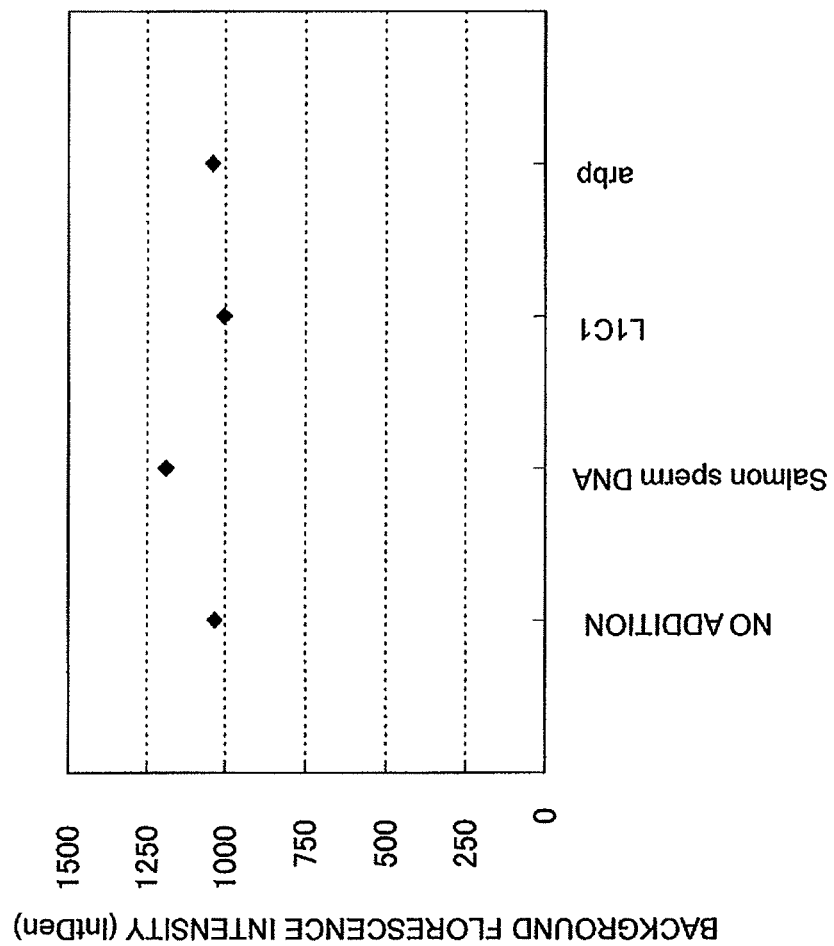
FIG. 5 represents the signal intensity calculated from the result of RNA in situ hybridization at a probe concentration of 0 nM in Example 2, determining the effects of adding two dummy oligo DNAs, salmon sperm DNA, and no components at each oligo DNA probe concentration.
Figure 6:
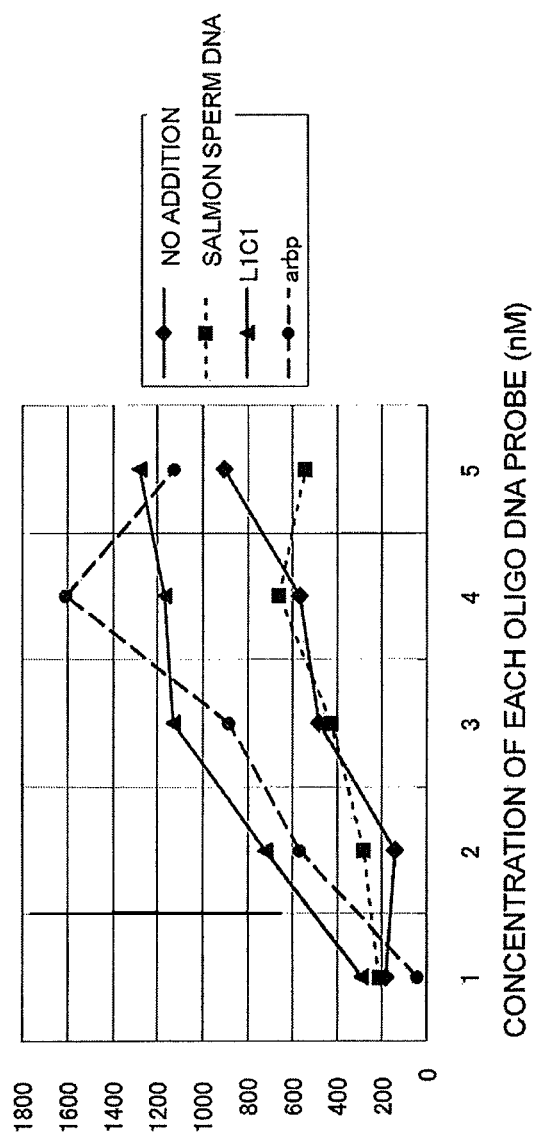
FIG. 6 represents the signal intensity calculated from the result of RNA in situ hybridization at each probe concentration in Example 2, determining the effects of adding two dummy oligo DNAs, salmon sperm DNA, and no components at each oligo DNA probe concentration.

Effectiveness for the RNA detection by quantitative RNA in situ hybridization was examined between dummy oligo DNA, salmon sperm DNA, and without the addition of these components. For the experiment, mouse liver tissue samples were prepared by formalin fixation and paraffin embedding, and serial sections were made as in Example 1. Further, as in Example 1, Cyp1a2 was used as the detected gene, and four single-stranded oligo DNA probes of SEQ ID NOS: 1 to 4 FITC-labeled at the both ends were used. Two dummy oligo DNAs (single-stranded) of SEQ ID NO: 5 (L1C1) and SEQ ID NO: 6 (arbp) were used at the concentrations with the addition ratio of 8 with respect to each different concentration 0 nM (nanomol), 1 nM, 2 nM, 3 nM, 4 nM, 5 nM of the four probes. Further, a salmon sperm DNA (Salmon Sperm DNA solution, catalog number 15632-011; Invitrogen) was added to each different oligo DNA probe concentration to make the final concentration 100 µg/ml (microgram/milliliter; equivalent of 80 nM). As a control, an experiment was conducted without adding the dummy oligo DNA or salmon sperm DNA ("no addition"). For the FITC label detection, the anti-FITC rabbit polyclonal antibody P5100 (Delco) was used, and TSA sensitization was performed using a tyramide-FLU (Perkin-Elmer, TSA Plus Fluorescein System, NEL741B001KT). FIG. 4 represents in situ hybridization images obtained from the same region of the serial sections. The images are for no addition, images with the addition of salmon sperm DNA, images with addition of dummy oligo DNA L1C1, and images with addition of dummy oligo DNA arbp, respectively, from above. The concentrations of the four oligo DNA probes are 0 nM (nanomol), 1 nM, 2 nM, 3 nM, 4 nM, and 5 nM from the left. The images were taken in the same regions of the serial sections with a 10× objective lens, using a Zeiss fluorescence microscope Axioplan2 and a CCD camera AxioCam. The images were computer processed using Image J software (NIH, http://rsb.info.nih.gov/ij/), and signal intensity was determined at each concentration. The image signal intensity is the background fluorescence intensity (IntDen) at the oligo DNA probe concentration of 0 nM. FIG. 5 represents the background fluorescence intensity for samples with no addition, and for samples with the addition of the salmon sperm DNA, and the dummy oligo DNAs L1C1 and arbp. The background fluorescence intensity is higher in samples with the addition of the salmon sperm DNA than in other samples. A true signal intensity at each concentration was determined by subtracting the background fluorescence intensity from the signal intensity of each different concentration. FIG. 6 represents the results. Samples with the addition of the dummy oligo DNA arbp at the oligo DNA probe concentration of 1 nM has a weaker true signal intensity than other samples. However, the fact that the signals are observed with good contrast suggests that the addition of the oligo DNA probes involves only a small increase in background noise. It can be seen from FIG. 6 that the addition of the dummy oligo DNA L1C1 or arbp produces a true signal about 1.4 to 2.5 times higher than that obtained with the salmon sperm DNA or in samples with no addition of these components (particularly at the probe concentrations of 2 nM and higher). It can also be seen that there is very good linearity between probe concentration and signal intensity in samples with the addition of the dummy oligo DNAs L1C1 and arbp.

EXAMPLE 3

Comparison Between Dummy Oligo DNA and Salmon Sperm DNA

Figure 7:
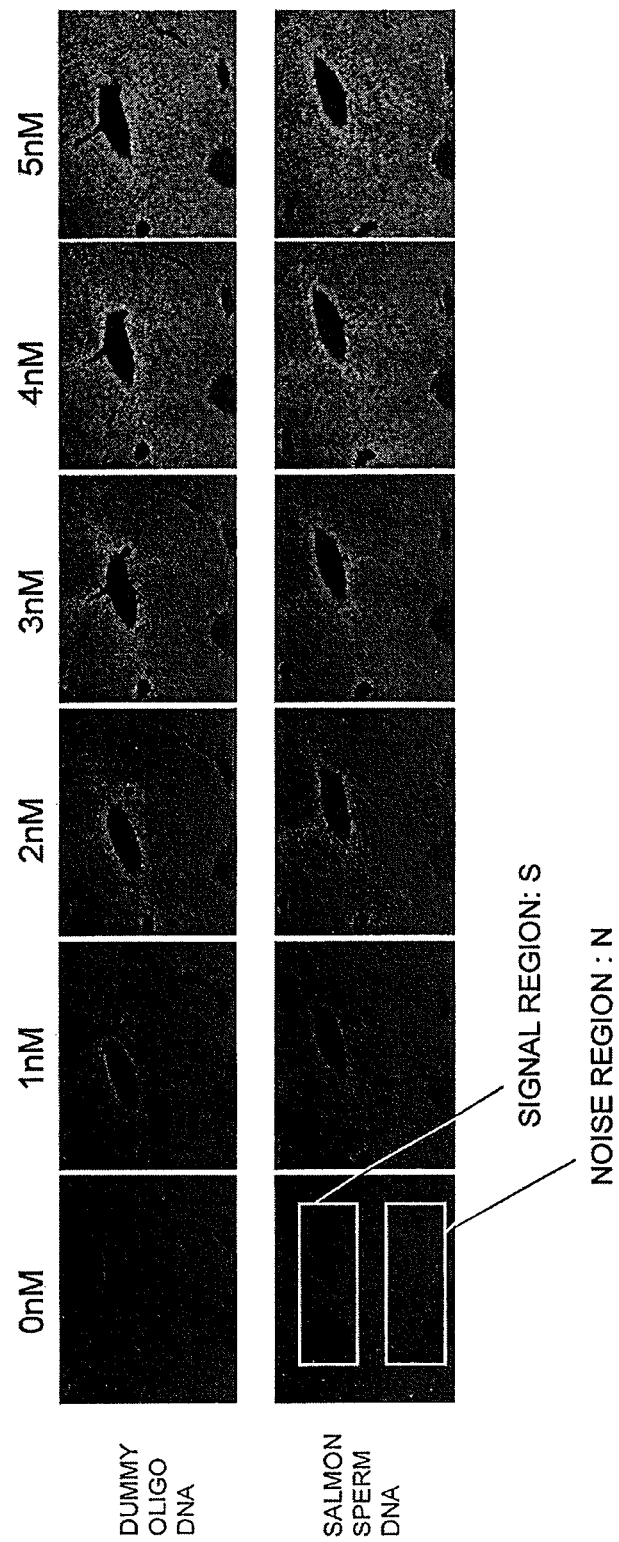
FIG. 7 represents the result of comparison between RNA in situ hybridizations using dummy oligo DNA and salmon sperm DNA with regard to effects on RNA detection in Example 3.
Figure 8:
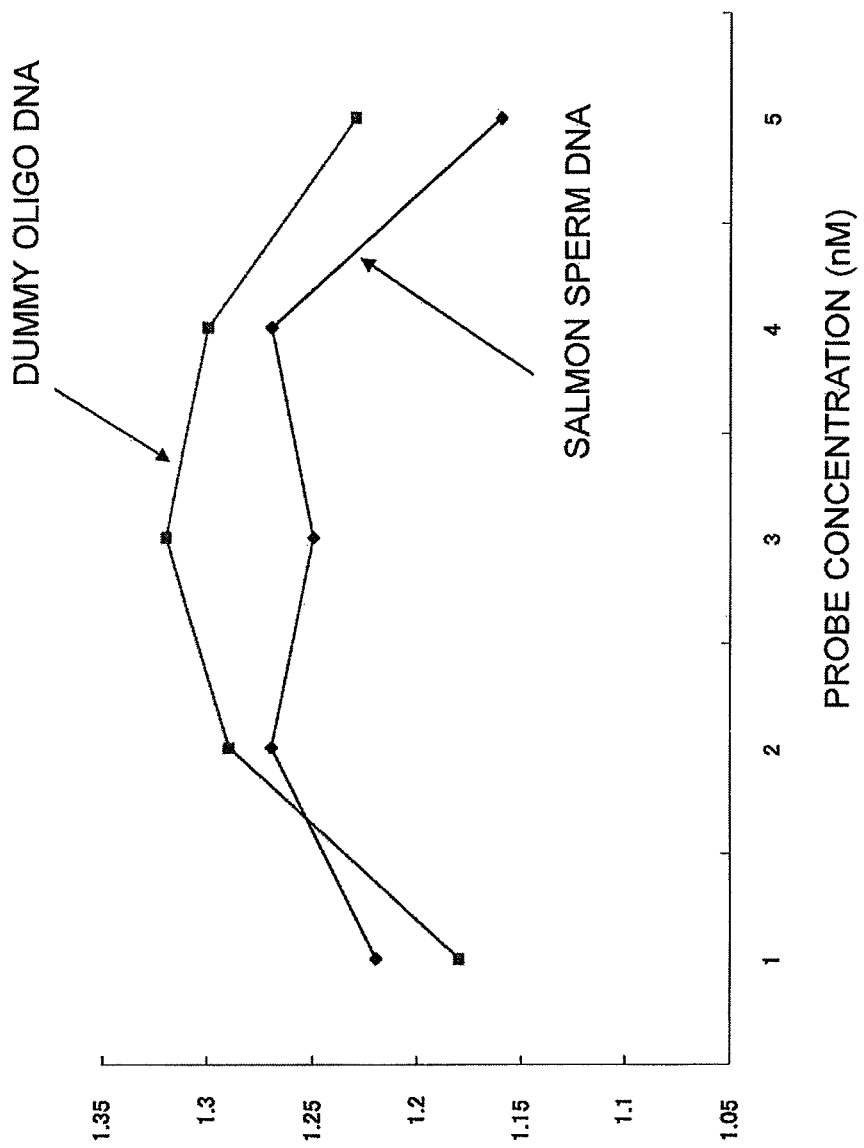
FIG. 8 is a graph representing the result of SN ratio comparison between dummy oligo DNA and salmon sperm DNA in Example 3, in which the vertical axis represents SN ratio, and the horizontal axis represents probe concentration.

Effectiveness for the RNA detection by quantitative RNA in situ hybridization was examined between dummy oligo DNA and salmon sperm DNA. For the experiment, mouse liver tissue samples were prepared by formalin fixation and paraffin embedding, and serial sections were made as in Example 1. Further, as in Example 1, Cyp1a2 was used as the detected gene, and four single-stranded oligo DNA probes of SEQ ID NOS: 1 to 4 FITC-labeled at the both ends were used. A dummy oligo DNA (single-stranded) of SEQ ID NO: 5 was used at the concentration with the addition ratio of 8 with respect to each different concentration 0 nM (nanomol), 1 nM, 2 nM, 3 nM, 4 nM, 5 nM of the four oligo DNA probes, Further, a salmon sperm DNA (Salmon Sperm DNA solution, catalog number 15632-011; Invitrogen) was added to each different probe concentration to make the final concentration 100 µg/ml (microgram/milliliter; equivalent of 80 nM). For the FITC label detection, the anti-FITC rabbit polyclonal antibody P5100 (Daco) was used, and sensitization was performed using a tyramide-FLU (Perkin-Elmer, TSA Plus Fluorescein System, NEL741B001KT). FIG. 7 represents in situ hybridization images obtained from the same region of the serial sections. The upper images are from samples with the addition of the dummy oligo DNA, the lower images from samples with the addition of the salmon sperm DNA. The concentrations of the four probes are 1 nM (nanomol), 2 nM, 3 nM, 4 nM, and 5 nM from the left. The images were taken in the same regions of the serial sections with a 10× objective lens, using a Zeiss fluorescence microscope Axioplan2 and a CCD camera AxioCam. In these images, a signal region S with signals, and a noise region N without signals were set as in FIG. 7, and the signal intensity of each region was determined using Image J software (NIH, http://rsb.info.nih.gov/ij/). The ratio of signal intensities in regions S and N was then determined as the SN ratio (signal-to-noise ratio). FIG. 8 compares the SN ratios for samples with the addition of the dummy oligo DNA and for samples with the addition of the salmon sperm DNA. The vertical axis represents SN ratio, and the horizontal axis represents probe concentration. As represented in FIG. 8, the relationship between oligo DNA probe concentration and SN ratio is bell shaped, with the dummy oligo DNA producing better SN ratios than the salmon sperm DNA at the oligo DNA probe concentrations of 2 nM and higher.

EXAMPLE 4

Dummy Oligo DNA Sequences

The type and number of dummy oligo DNA sequences were tested in this Example. For the experiment, mouse liver tissue samples were prepared by formalin fixation and paraffin embedding, and serial sections were made as in Example 1. Following deparaffinization, the specimens were treated with Protease K (Invitrogen, Proteinase K SOL. RNA, 25530049), and RNA in situ hybridization was performed, as in Example 1. Further, as in Example 1, Cyp1a2 was used as the detected gene, and single-stranded oligo DNA probes of SEQ ID NOS: 1 to 4 FITC-labeled at the both ends were used. In accord with the result of Example 2, the four probes were used at the concentration of 2 nM (nanomol). In the experiment, dummy oligo DNA (single-stranded) sequences L1W1, L1W2, L1W3 (SEQ ID NOS: 5, 7, and 8) and L1W1, L1W2, L1W3 (SEQ ID NOS: 9 to 11) were used in the following groups;

Individual sequences (L1C1, L1C2, L1C3; group ID=1)
Individual sequences (L1W1, L1W2, L1W3; group ID=2)
Mixtures of two sequences (an L1C1 and L1W1 mixture, an L1C2 and L1W2 mixture, and an L1C3 and L1W3 mixture; group ID=5)
A mixture of three sequences (an L1C1, L1C2, and L1C3 mixture; group ID=3)
A mixture of three sequences (an L1W1, L1W2, and L1W3 mixture; group ID=4)
A mixture of six sequences (group ID=6)

Figure 9:
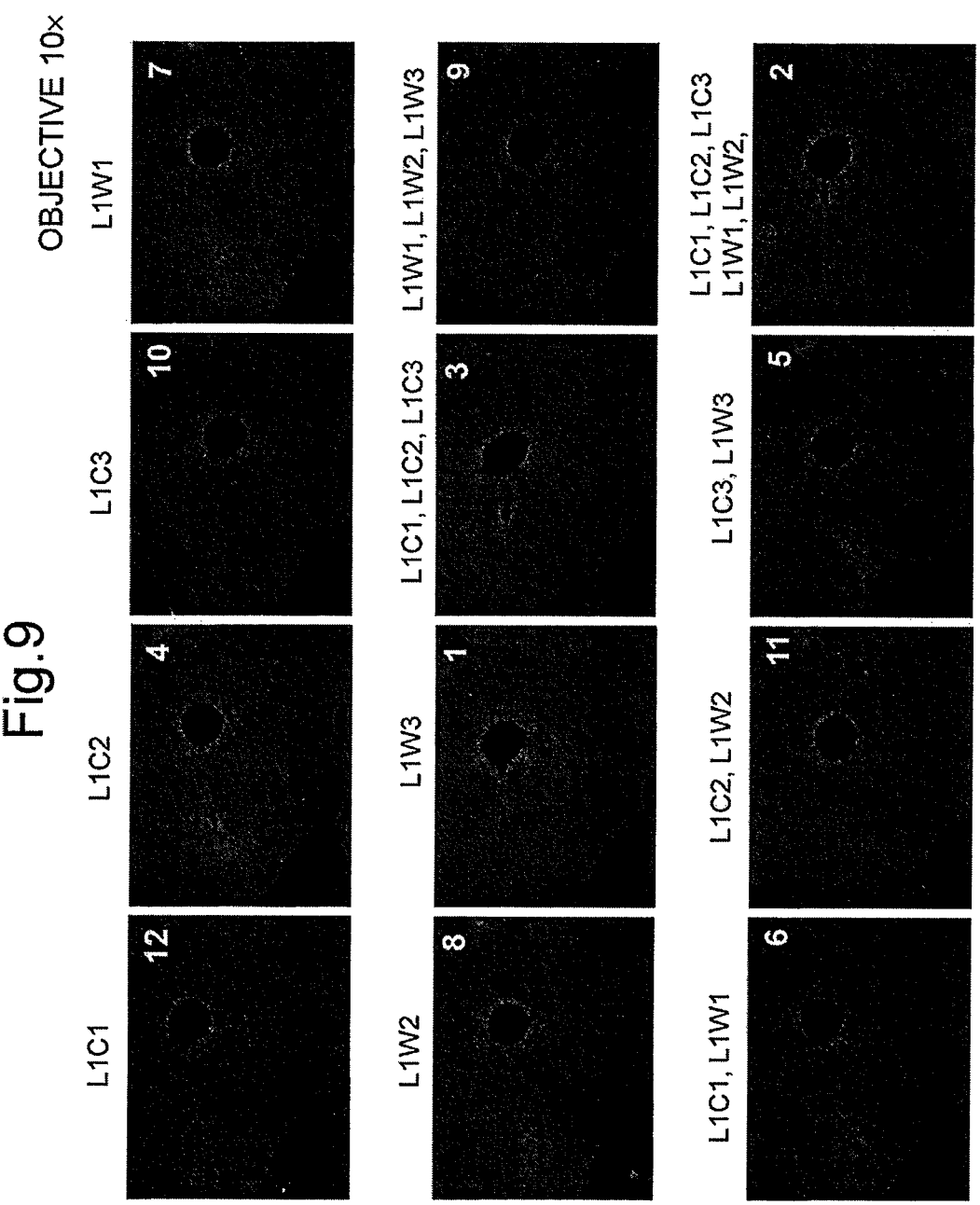
FIG. 9 represents the results of RNA in situ hybridizations performed with different types and numbers of dummy oligo DNA sequences in Example 4.
Figure 10:
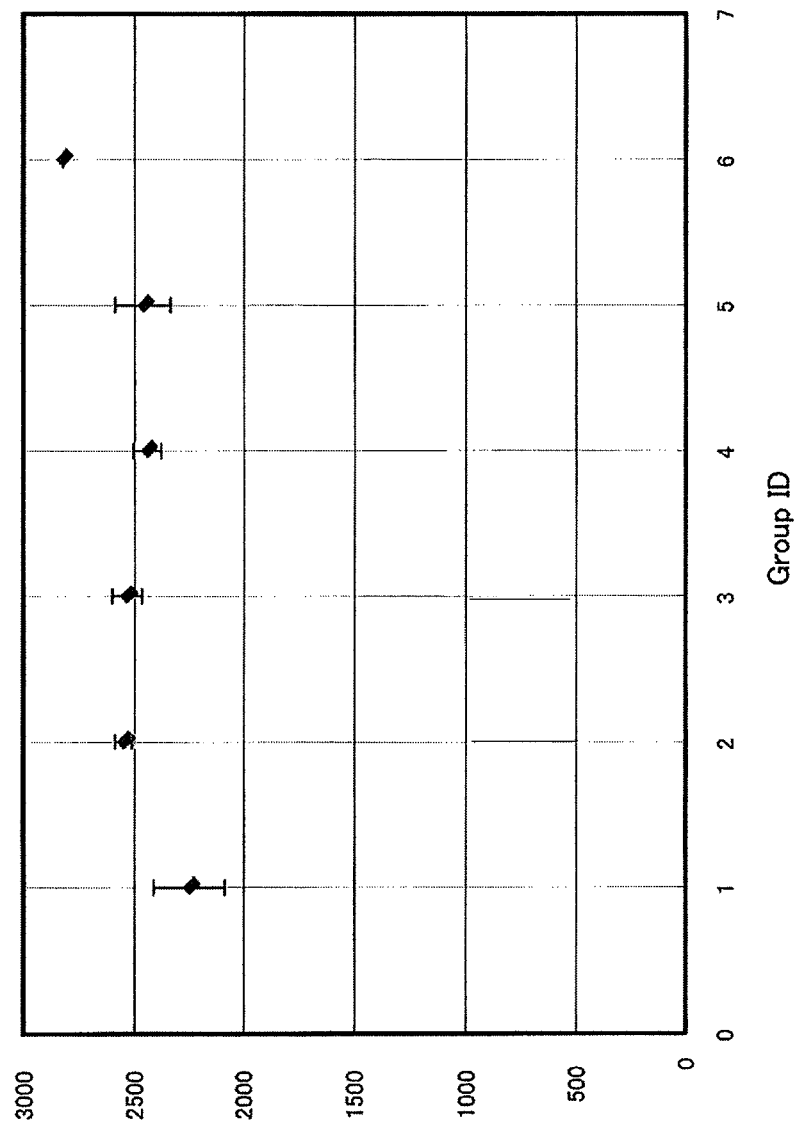
FIG. 10 represents the effect of each dummy oligo DNA determined as signal intensity from the results of RNA in situ hybridizations performed to determine the effects of various dummy oligo DNAs in Example 4.

Note that the sequences L1W1, L1W2, and L1W3 are the complementary sequences of L1W1, L1W2, and L1W3, respectively. The total concentration of the dummy oligo DNAs was 64 nM (the sum of the concentration 2 nM of each oligo DNA probe=8 nM, multiplied by 8). For the FITC label detection, the anti-FITC rabbit polyclonal antibody P5100 (Dako) was used, and sensitization was performed using a tyramide-FLU (Perkin-Elmer, TSA Plus Fluorescein System, NEL741B001KT). Images were taken in the same regions of the serial sections (the number at the top right of each image indicates the order of the serial sections) with a 10× objective lens, using a Zeiss fluorescence microscope Axioplan2 and a CCD camera AxioCam. FIG. 9 represents the results of RNA in situ hybridization. As represented in FIG. 9, desirable images were obtained in all combinations of the dummy oligo DNAs, except for the mixture of six dummy oligo DNAs producing poorer contrast than the other samples. The signal intensity of each region was determined using Image J software (NIH, http://rsb.info.nih.gov/ij/). The results are presented in FIG. 10 and Table 1. As shown in FIG. 10, there is no large difference in signal intensity between different types or combinations of the dummy oligo DNAs used, and the results are desirable.

TABLE 1

| Dummy oligo DNA | IntDen | Group ID | group a.v. | group s.d. |
|---|---|---|---|---|
| L1C1 | 2196.302 | 1 | 2249.49 | 162.96 |
| L1C2 | 2432.394 | | | |
| L1C3 | 2119.767 | | | |
| L1W1 | 2572.024 | 2 | 2547.47 | 34.298 |
| L1W2 | 2508.280 | | | |
| L1W3 | 2562.096 | | | |
| L1C1, C2, C3 | 2532.915 | 3 | 2532.92 | 64.242 |
| L1W1, W2, W3 | 2442.063 | 4 | 2442.06 | 64.242 |
| L1C1, W1 | 2398.463 | 5 | 2459.60 | 124.27 |
| L1C2, W2 | 2602.592 | | | |
| L1C3, W3 | 2377.751 | | | |
| L1C1, C2, C3, W1, W2, W3 | 2823.044 | 6 | 2823.04 | 0 |

EXAMPLE 5

Number of Probes and Signal Intensity

The relationship between the number of probes used for detection and the detected signal intensity was examined in this Example. Theoretically, when the hybridization oligonucleic acid probes in a hybridization solution have a uniform concentration and a GC content of 50%, the equilibrium constant K is the same for all the oligonucleic acid probes undergoing the hybridization process, and the following relation is established for oligonucleic acid probe i.

$$K=[Hi]/[fR]\cdot[fPi] \quad \text{(Equation 1)}$$

The free oligonucleic acid probe concentration [fPi] is the same for all the oligonucleic acid probes.

The hybridization amount (concentration) Hi of the oligonucleic acid probe i is given by $$[Hi]=K\cdot[fR]\cdot[fPi] \quad \text{(Equation 2), and}$$

$$[H1]=[H2]=\ldots=[HN] \quad \text{(Equation 3).}$$

It follows from this that the observed signal intensity I is additive as represented by $$I=S([H1])+\ldots+S([HN]) \quad \text{(Equation 4).}$$

The signal intensity I thus increases as an increasing function of (theoretically, in proportion to) the number N of the oligonucleic acid probes in the hybridization solution.

Figure 11:
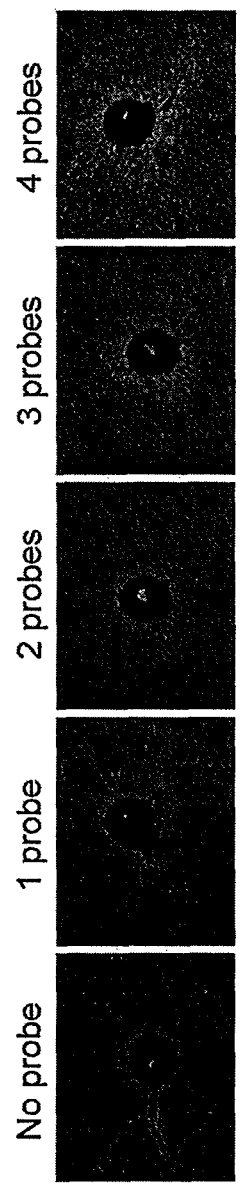
FIG. 11 represents the RNA in situ hybridization photographic images representing the relationship between signal intensity and the number of probes used for the detection in Example 5.
Figure 12:
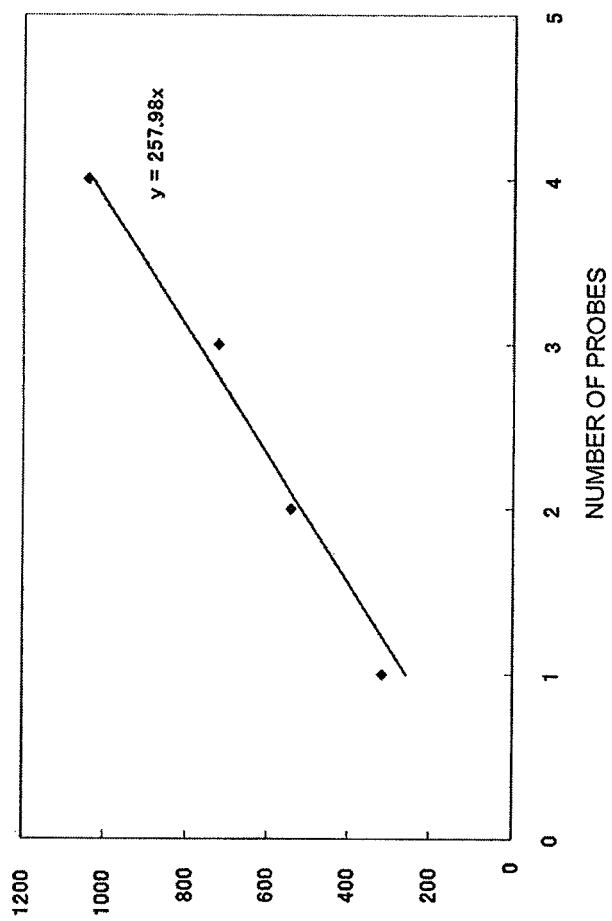
FIG. 12 represents the correlation between signal intensity and the number of probes in Example 5.

For the experiment, mouse liver tissue samples were prepared by formalin fixation and paraffin embedding, and serial sections were made as in Example 1. Following deparaffinization, the specimens were treated with Protease K (Invitrogen, Proteinase K SQL. RNA, 25530049), and RNA in situ hybridization was performed, as in Example 1. Further, as in Example 1, Cyp1a2 was used as the detected gene, and single-stranded oligo DNA probes of SEQ ID NOS: 1 to 4 FITC-labeled at the both ends were used. The four oligo DNA probes were used at the concentration of 2 nM (nanomol), and experiments were performed with one, two, three, and four oligo DNA probes, and without the oligo DNA probe. A dummy oligo DNA (L1C1) of SEQ ID NO: 5 was used as the dummy oligo DNA (single-stranded) at a concentration 8 times the total concentration of the oligo DNA probes used. Specifically, the concentration of the dummy oligo DNA was 16 nM, 32 nM, 48 nM, and 64 nM for one, two, three, and four oligo DNA probes, respectively. The concentration of the dummy oligo DNA was 64 nM for samples with no oligo DNA probe. For the FITC label detection, the anti-FITC rabbit polyclonal antibody P5100 (Dako) was used, and sensitization was performed using a tyramide-FLU (Perkin-Elmer, TSA Plus Fluorescein System, NEL741B001KT). Images were taken in the same regions of the serial sections with a 10× objective lens, using a Zeiss fluorescence microscope Axioplan2 and a CCD camera AxioCam. The images are shown in FIG. 11. The signal intensity of each image was determined using Image J software (NIH, http://rsb.info.nih.gov/ij/), and the value obtained by subtracting the signal intensity of the image without the oligo DNA probe from this preliminary signal intensity was determined as the signal intensity of the image using each number of probe. The results are plotted in FIG. 12, in which the vertical axis represents signal intensity, and the horizontal axis represents the number of oligo DNA probes. As shown in the figure, with the addition of the dummy oligo DNA, the relationship between the number of oligo DNA probes and signal intensity is linear, producing a definite, upward straight line.

EXAMPLE 6

Probe Concentration

Changes in signal intensity with increase in the concentration of the oligo DNA probe used for detection were examined.

Hybridization is a type of equilibrium reaction, and, theoretically, the following relation is established.

$$K=[H]/[fR]\cdot[fP],$$

where K is the equilibrium constant, [H] is the concentration of a hybridized product, [fR] is the free mRNA concentration, and [fP] is the free oligo DNA probe concentration.

Because the relation P0=[H]+[fP] for the concentration of the hybridized oligo DNA probe, and the relation R0=[H]+[fR] for the mRNA concentration in a tissue sample (constant in the tissue sample are true), the hybridized product increases as the concentration of the hybridized oligo DNA probe is increased. This Example demonstrates that the signal intensity also increases linearly with increasing oligo DNA probe concentrations.

Figure 13:
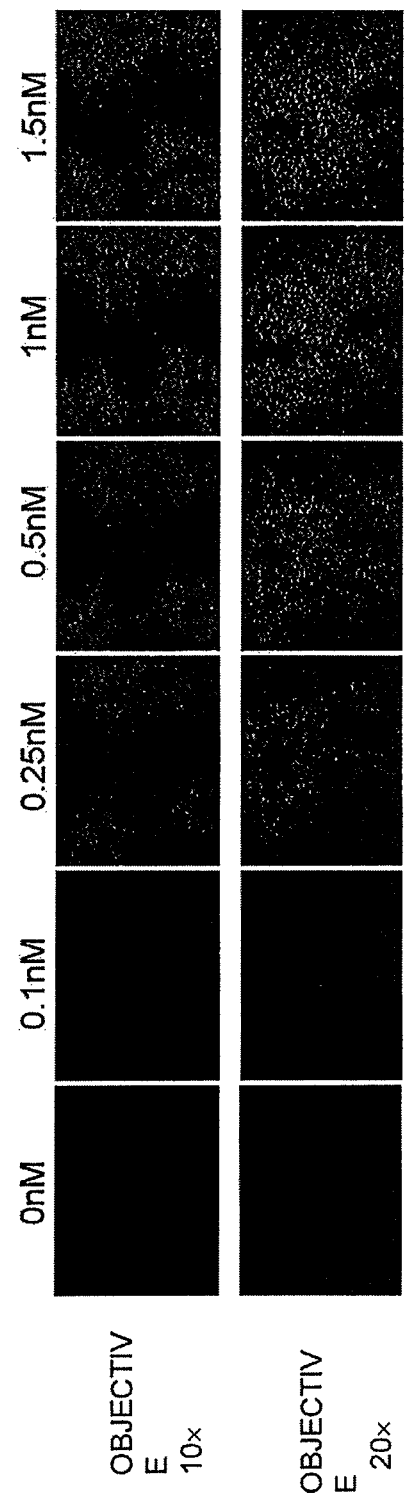
FIG. 13 represents photographic images showing how signal intensity varies with increasing concentrations of the probe used for the detection in Example 6.
Figure 14B:
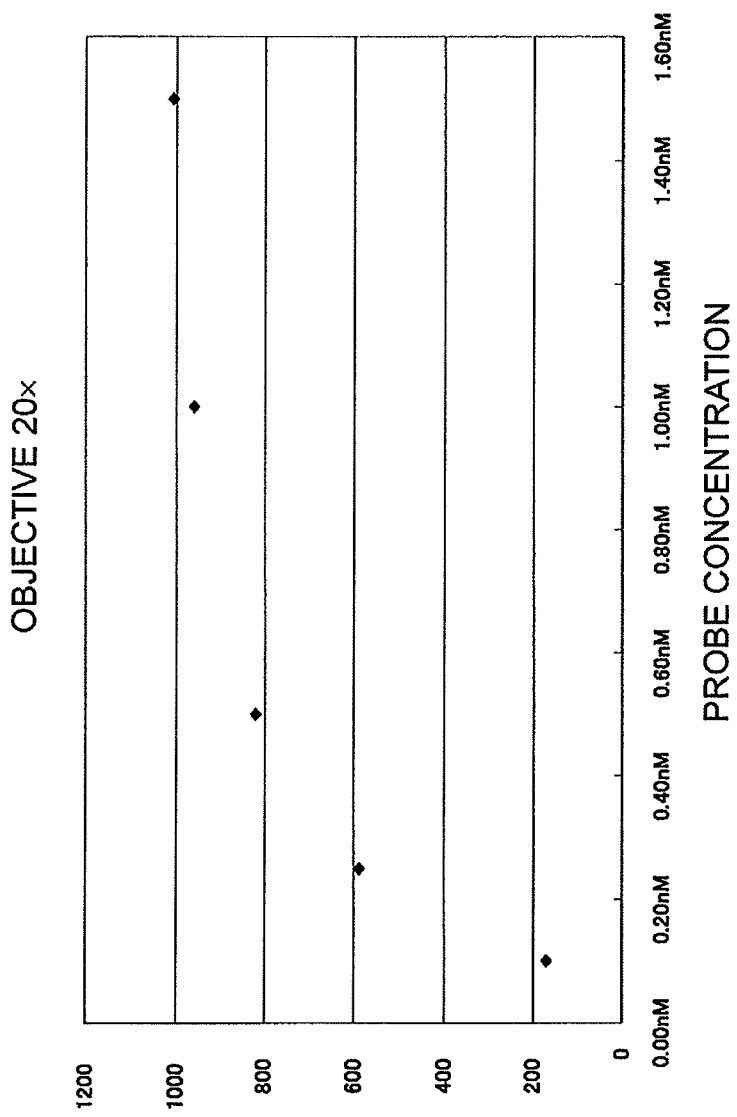
FIG. 14b represents the correlation between signal intensity and probe concentration in Example 6.

For the experiment, mouse liver tissue samples were prepared by formalin fixation and paraffin embedding, and serial sections were made as in Example 1. Following deparaffinization, the specimens were treated with Protease K (Invitrogen, Proteinase K SOL, RNA, 25530049), and RNA in situ hybridization was performed, as in Example 1, Albumin Alb was used as the detected gene, and a single-stranded oligo DNA probe of SEQ ID NO: 12 FITC-labeled at the both ends was used in six different concentrations 0 nM (no probe), 0.1 nM, 0.25 nM, 0.5 nM, 1 nM, and 1.5 nM. A dummy oligo DNA (single-stranded) of SEQ ID NO: 5 was used as the dummy oligo DNA at a concentration 8 times the concentration of the oligo DNA probe used. A 12 nM dummy oligo DNA was used in a hybridization solution that contained no oligo DNA probe. For the FITC label detection, the anti-FITC rabbit polyclonal antibody P5100 (Dako) was used, and sensitization was performed using a tyramide-FLU (Perkin-Elmer, TSA Plus Fluorescein System, NEL741B001KT). Images were taken in the same regions of the serial sections with an objective lens (10× and 20×), using a Zeiss fluorescence microscope Axioplan2 and a CCD camera AxioCam. The images are shown in FIG. 13. The images are shown in FIG. 13 (the upper images with a 10× objective lens, and the lower images with a 20× objective lens). The signal intensity of the image at each concentration was determined using a computer with Image J software (NIH, http://rsb.info.nih.gov/ij/), and the value obtained by subtracting the signal intensity of the image at the oligo DNA probe concentration 0 nM from the computed signal intensity was determined as the true signal intensity. The results are plotted in FIG. 14, in which the vertical axis represents signal intensity, and the horizontal axis represents probe concentration (FIG. 14a represents the signal intensity for the images taken with a 10× objective lens shown in FIG. 13, and FIG. 14b represents the signal intensity for the images taken with a 20× objective lens shown in FIG. 13). As shown in the figure, the signal intensity linearly increases with increasing probe concentrations, before saturating above a certain concentration (1 nM in the case of Alb gene in FIG. 14). The result is the reflection of very high expression levels of Alb gene in the liver, as demonstrated by the result of quantitative PCR in Example 9.

EXAMPLE 7

Probe Concentration

Figure 15:
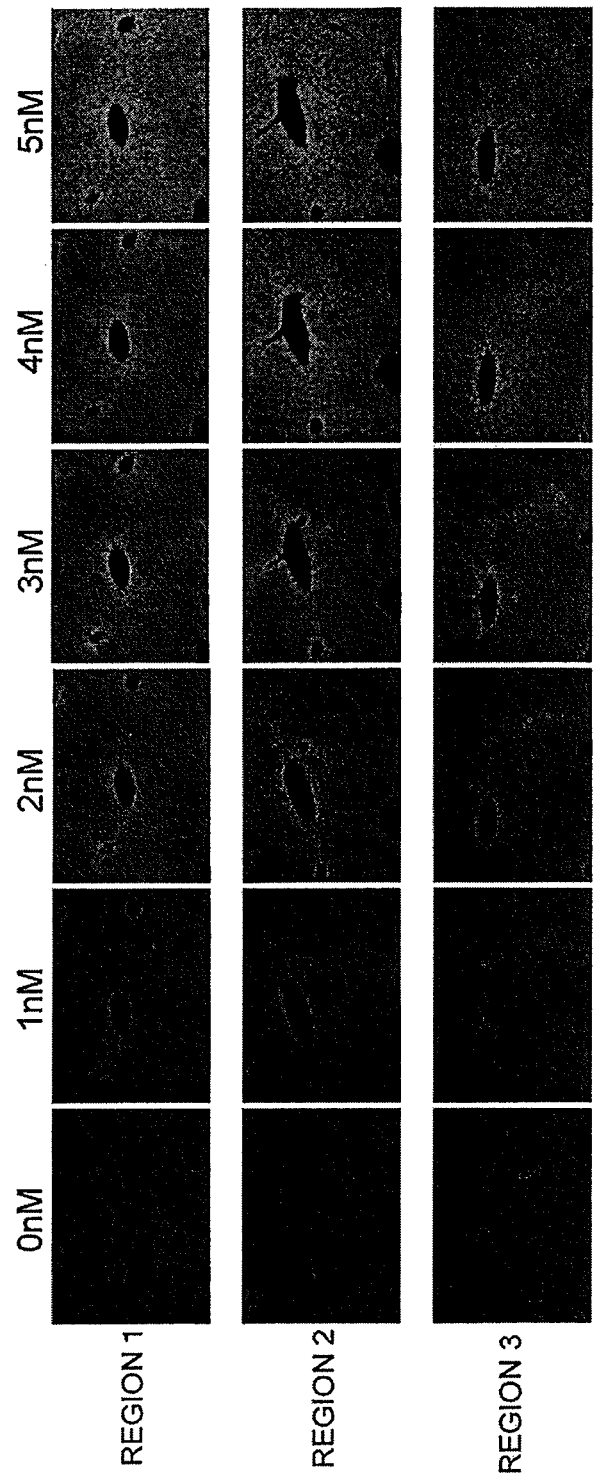
FIG. 15 represents photographic images showing how signal intensity varies with increasing concentrations of the probe used for the detection in Example 7.
Figure 16:
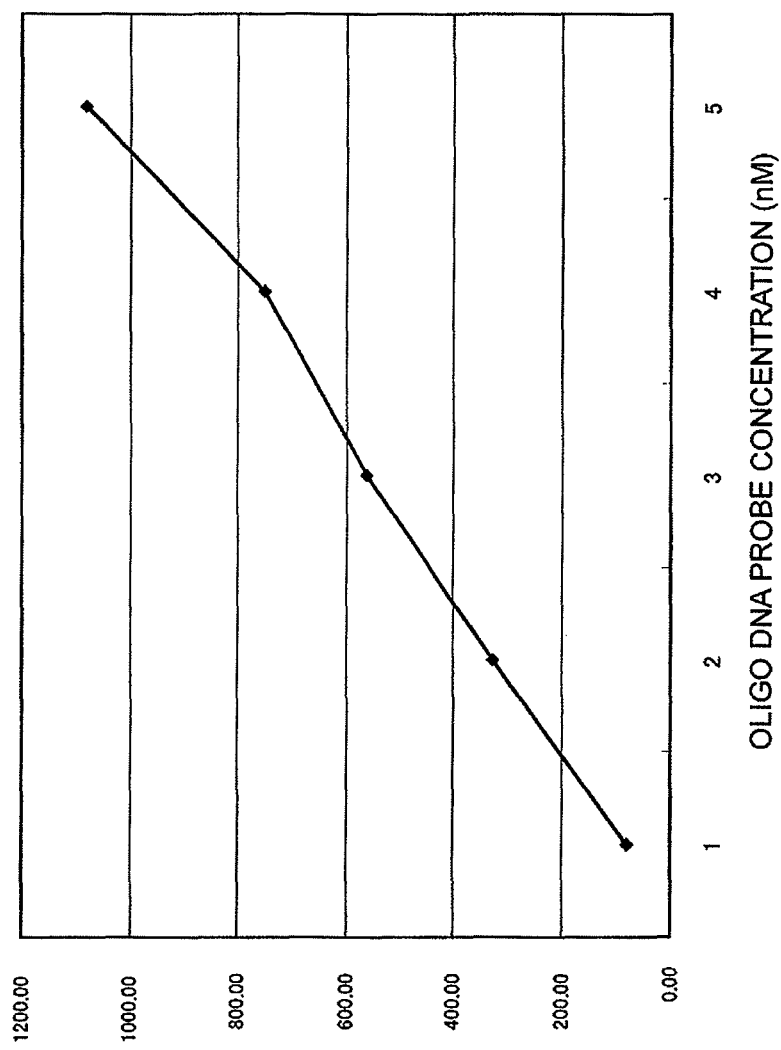
FIG. 16 represents the correlation between signal intensity and probe concentration in Example 7.

Changes in signal intensity with increasing concentrations of the probes used for detection were examined. For the experiment, mouse liver tissue samples were prepared by formalin fixation and paraffin embedding, and serial sections were made as in Example 1. Following deparaffinization, the specimens were treated with Protease K (Invitrogen, Proteinase K SOL. RNA, 25530049), and RNA in situ hybridization was performed, as in Example 1. As in Examples 1 and 2, Cyp1a2 was used as the detected gene, and single-stranded oligo DNA probes of SEQ ID NO: 1 to 4 FITC-labeled at the both ends were used. A dummy oligo DNA (single-stranded) of SEQ ID NO: 5 at the concentration with the addition ratio of 8 with respect to each different concentration 0 nM (nanomol), 1 nM, 2 nM, 3 nM, 4 nM, 5 nM of the four oligo DNA probes was used. The dummy oligo DNA was used at the concentration of 64 nM for a hybridization solution that contained no oligo DNA probe. For the FITC label detection, the anti-FITC rabbit polyclonal antibody P5100 (Dako) was used, and sensitization was performed using a tyramide-FLU (Perkin-Elmer, TSA Plus Fluorescein System, NEL741B001KT). Images were taken at the three locations in the same regions of the serial sections with a 10× objective lens, using a Zeiss fluorescence microscope Axioplan2 and a CCD camera AxioCam. The images are shown in FIG. 15. The signal intensity of the image at each concentration was determined using a computer with Image J software (NIH, http://rsb.info.nih.gov/ij/). The value obtained by subtracting the signal intensity of the image at the probe concentration 0 nM from the computed signal intensity was determined as the true signal intensity, and a mean value of the three points was determined. The result is plotted in FIG. 16, in which the vertical axis represents signal intensity, and the horizontal axis represents probe concentration. As shown in the figure, the signal intensity also increases linearly with increase in probe concentration in the presence of the dummy oligo DNA.

EXAMPLE 8

Expression Level and Signal Intensity

This Example demonstrates that there is a linear relationship between expression level and signal intensity, and that quantitative detection of the target gene mRNA is therefore possible with the RNA in situ hybridization of the present invention. In this Example, Arntl that changes its expression levels according to the circadian cycle was used as the detected gene. Male mice, 8 weeks of age, were used, and the subject tissue liver (lateral left lobe) was collected from each group of two individuals at five time points separated by 4 hours from 9 a.m. to 1 a.m. (hour 25). The tissue was cut in half, and 2-mm regions on the both sides of the cross section were used as a sample tissue for formalin fixation and paraffin embedding, and an RNA extraction tissue sample for quantitative PCR, respectively.

Tissue samples were prepared by formalin fixation and paraffin embedding, and serial sections were made as in Example 1. Following deparaffinization, the specimens were treated with Protease K (Invitrogen, Proteinase K SOL. RNA, 25530049), and RNA in situ hybridization experiment was performed, as in Example 1. Single-stranded oligo DNA probes of SEQ ID NOS: 13 and 14 Dig-labeled at the both ends were used as the oligonucleic acid probes for the detected gene Arntl (21 bases on the Arntl gene mRNA). Each probe was used at the concentration of 2 nM (nanomol). L1C1 of SEQ ID NO: 5 was used as the dummy oligo DNA (single-stranded) at the concentration with the addition ratio of 8. For the Dig label detection, the anti-Dig antibody (Roche; anti-digoxigenin-POD, 1207733) was used, and TSA sensitization was performed using a tyramide-Cy3 (Perkin-Elmer; TSA Plus Cyanine 3 System, NEL744B001KT). Images were taken with a 10× objective lens, using a Zeiss fluorescence microscope Axioplan2 and a CCD camera AxioCam.

Figure 17:
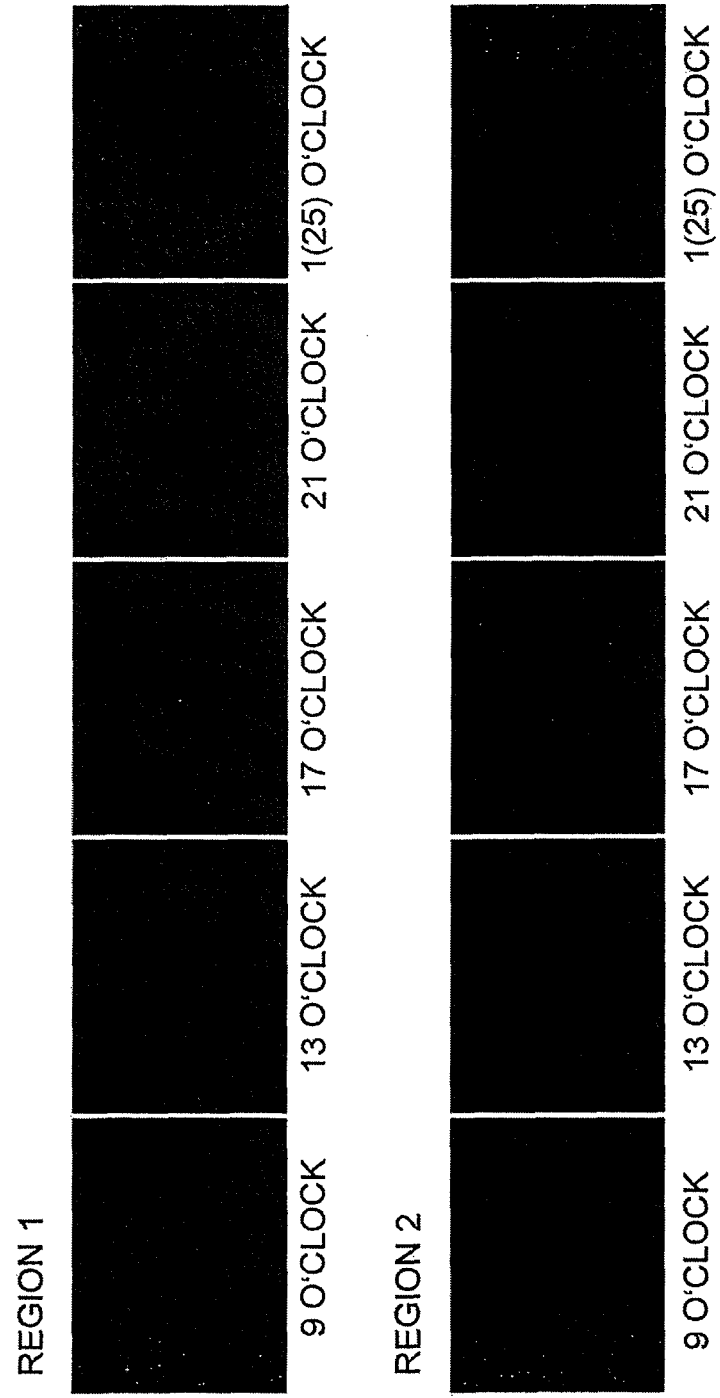
FIG. 17 represents the photographic images representing circadian cycle-dependent changes in the expression of Arntl gene as determined for the mouse liver by RNA in situ hybridization at the time intervals of 4 hours from 9 a.m. to 1 a.m. in Example 8.
Figure 18:
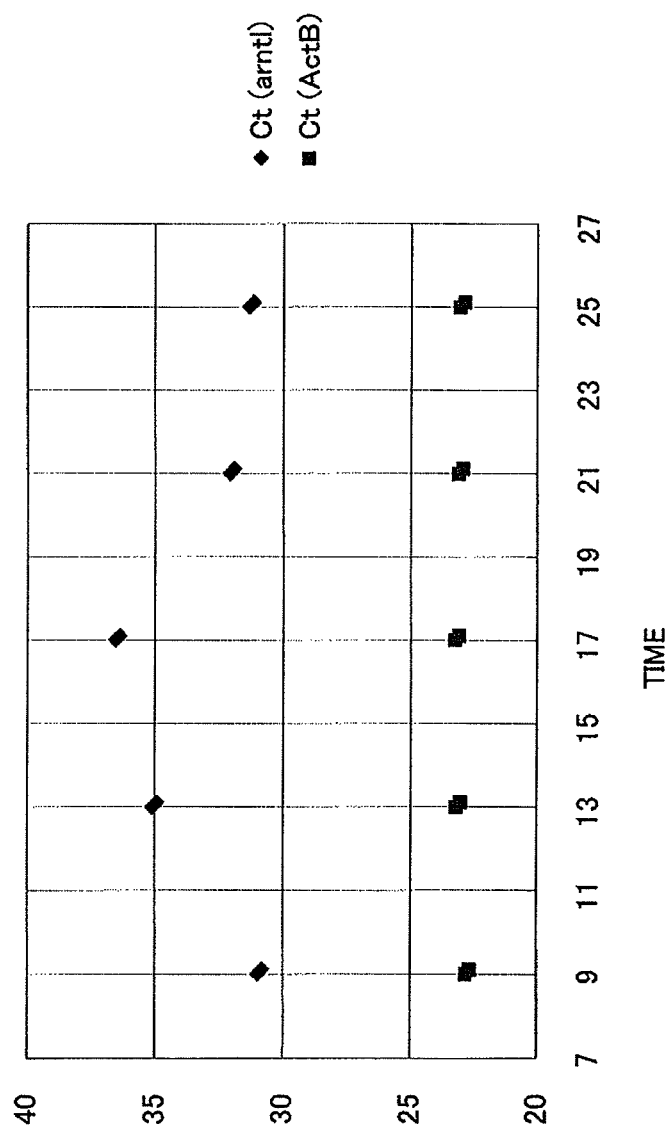
FIG. 18 represents changes in the expression level of internal standard gene Actb and circadian cycle-dependent changes in the expression level of Arntl gene, as determined by quantitative PCR for the liver collected at the time intervals of 4 hours from 9 a.m. to 1 a.m, in Example 8.
Figure 19:
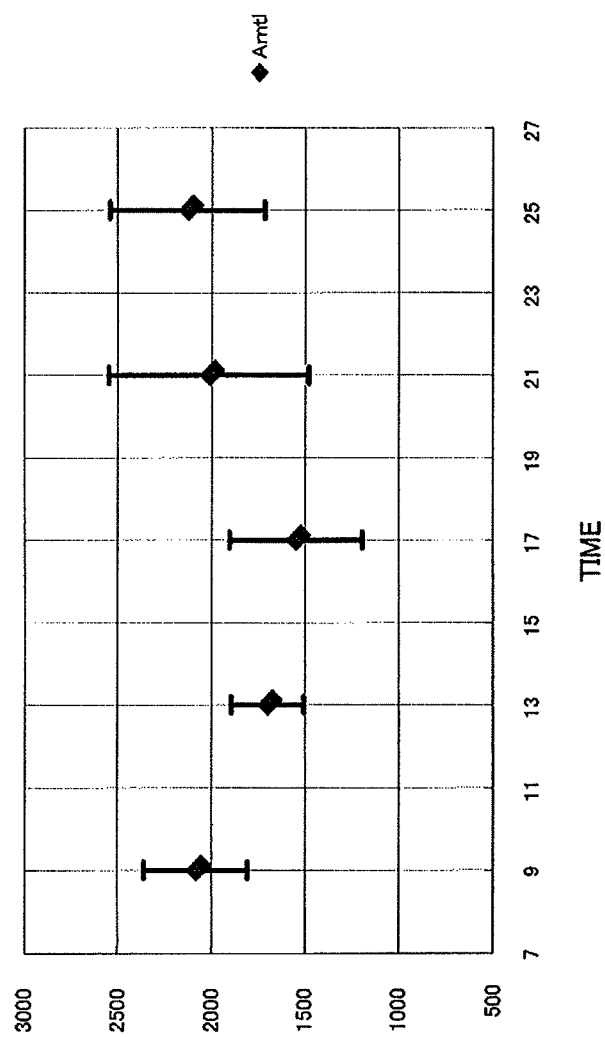
FIG. 19 represents changes in signal intensity as determined by monitoring changes in the expression of Arntl gene in liver by RNA in situ hybridization at the time intervals of 4 hours from 9 a.m. to 1 a.m. in Example 8.
Figure 20:
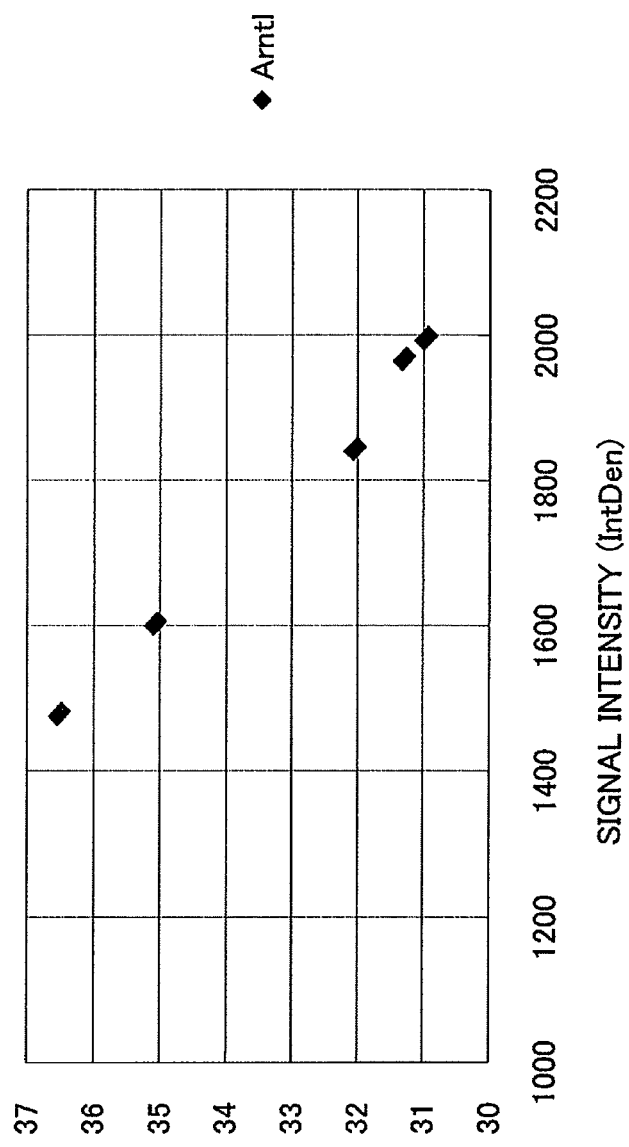
FIG. 20 represents the correlation between the result of quantitative PCR and signal intensity based on the results of quantitative PCR and RNA in situ hybridization performed to examine changes in the expression of Arntl gene in liver at the time intervals of 4 hours from 9 a.m. to 1 a.m. in Example 8.

FIG. 17 shows images of two regions of the liver of a single individual at each time point. The signal intensity of the image at each time point was determined using a computer with Image J software (NIH, http://rsb.info.nih.gov/ij/), and the values were compared with the expression levels found by quantitative PCR. The expression levels of Arntl gene mRNA were measured by quantitative PCR using forward and reverse primers of SEQ ID NOS: 15 and 16, according to the TaqMan method. The sequence of the TaqMan probe is represented by SEQ ID NO: 17. Quantitative PCR was simultaneously performed also for the internal standard gene Actb (PCR primers and the TaqMan probe for Actb were purchased from Applied Biosystems). The quantitative PCR was performed using a 7500 Reat-time PCR System (Applied Biosystems), according to the accompanying protocol. FIG. 18 represents changes in the expression levels of the target gene Arntl and Actb in tissue samples collected every 4 hour. The values are shown as changes in Ct values determined by quantitative PCR. FIG. 19 represents changes in signal intensity determined by the RNA in situ hybridization for the target gene Arntl. FIG. 20 represents the relationship between quantitative PCR Ct value and RNA in situ hybridization signal intensity. In the figure, the Ct values determined by the quantitative PCR for the target gene Arntl in the liver collected from each individual are plotted against the mean values in each time group of the signal intensities determined by RNA in situ hybridization. As represented in FIG. 20, there is a good correlation between the quantitative PCR Ct value and the signal intensity in the presence of the dummy oligo DNA (the correlation has a downward slope when the Ct value and the signal intensity are plotted on the vertical and horizontal axes as in the figure, because the Ct value decreases with increase in mRNA expression levels).

EXAMPLE 9

Expression Level and Signal Intensity, Two Colors

The liver of an individual male mouse, 8 weeks of age, collected at 1 p.m. in Example 8 was used as the tissue sample. TSA sensitization was performed stepwise, using oligo DNA probes Dig-labeled at the both ends for the target gene Cyp1a2, and oligo DNA probes FITC-labeled at the both ends for the target gene Alb. The quantitative detection of these two target genes was performed with the fluorescent dyes of two colors, and the detection results were compared with the Ct values obtained by the quantitative PCR for these genes.

The expression levels of the Cyp1a2 gene mRNA were quantified by quantitative PCR using the forward and reverse primers represented by SEQ ID NOS: 18 and 19, according to the TaqMan method. The sequence of the TaqMan probe is represented by SEQ ID NO: 20. The expression levels of the Alb gene mRNA were quantified by quantitative PCR using the forward and reverse primers represented by SEQ ID NOS: 21 and 22, according to the TaqMan method. The sequence of the TaqMan probe is represented by SEQ ID NO: 23. The quantitative PCR was performed with a 7500 Reat-time PCR System (Applied Biosystems), according the accompanying protocol. The Ct value of the Alb gene was 22.135 (amplification efficiency 1.0178), whereas that of the Cyp1a2 gene was 27.053 (amplification efficiency 1.0008), demonstrating that the expression levels of the Alb gene were about $2^5$ times, specifically, about 128 times higher.

Five oligo DNA probes (a set of probes represented by SEQ ID NO: 2 and SEQ ID NOS: 24 to 27) Dig-labeled at the both ends, or an oligo DNA probe represented by SEQ ID NO: 2 were used for the Cyp1a2 gene. Two oligo DNA probes represented by SEQ ID NOS: 12 and 28 FITC-labeled at the both ends were used for the Alb gene. L1C1 represented by SEQ ID NO: 5 was used for the dummy oligo DNA. In the experiment, the mouse liver was prepared into serial sections after usual formalin fixation and paraffin embedding. Following deparaffinization, the specimens were treated with Protease K (Invitrogen, Proteinase K SOL. RNA, 25530049), and RNA in situ hybridization was performed using the probe mixture. For the Dig label detection, the anti-Dig antibody (Roche; anti-digoxigenin-POD, 1207733) was used, and TSA sensitization was performed using a tyramide-Cy3 (Perkin-Elmer; TSA Plus Cyanine 3 System, NEL744B001KT). For the FITC label detection, the anti-FITC rabbit polyclonal antibody P5100 (Dako) was used, and TSA sensitization was performed using a tyramide-FLU (Perkin-Elmer, TSA Plus Fluorescein System, NEL741B001KT). Micrographs were taken with a 10× objective lens, using a Zeiss fluorescence microscope Axioplan2 and a CCD camera AxioCam.

Figure 21:
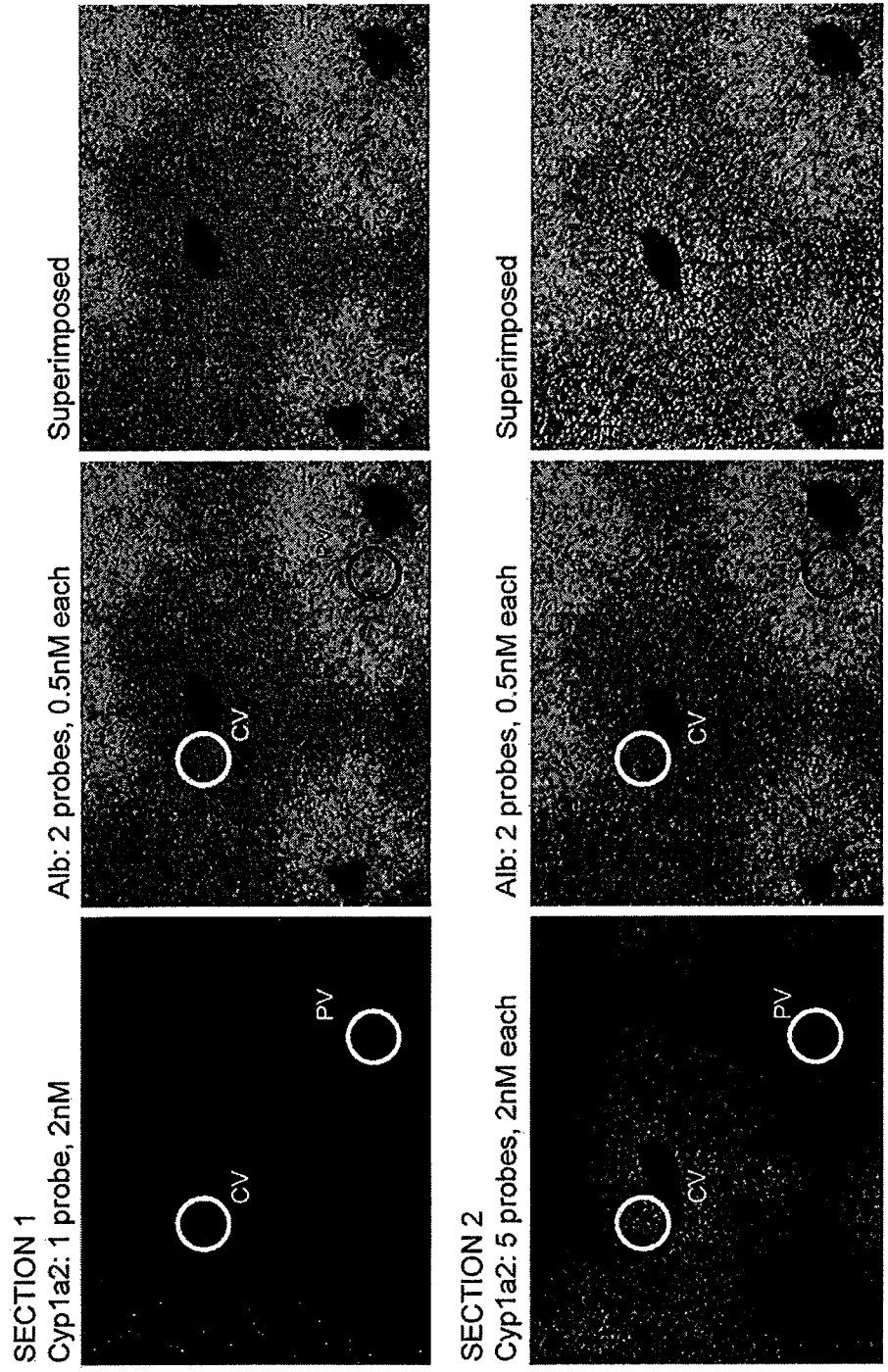
FIG. 21 represents the photographic images obtained by RNA in situ hybridizations simultaneously performed with more than one oligo DNA probe to determine the expression of Cyp1a2 and Alb genes in liver in Example 9.

The result of quantitative PCR revealed that the expression level of the Cyp1a2 gene was only about $1/128$ of the Alb gene. For example, FIG. 19 shows Cyp1a2 gene mRNA and Alb gene mRNA detected by Cy3 and FLU, respectively, in the same section using two serial sections. In FIG. 21, the upper in situ hybridization images are results obtained by using a single probe for the Cyp1a2 gene detection (section 1), and the lower images are results from using the five probes (section 2). As can be seen from the figure, the expression of the two genes is localized differently, the Alb gene being expressed in the PV (portal vein) region, and the Cyp1a2 gene being expressed at the CV (central vein) region. Signals are considerably weak in the detection of Cyp1a2 gene mRNA when only one probe is used. However, with five probes, the signal intensity approaches the signal intensity of the Alb gene mRNA detected by FLU. Specifically, despite about $1/128$ of the Cyp1a2 gene expression compared with the Alb gene in the quantitative PCR, it was possible to overcome the $10^2$-fold expression level difference, and to successfully increase the signal intensity by increasing the number of probes. Table 2 summarizes the results with the FLU and Cy3 signal intensities measured in eight small circular regions of the size set for each of the PV and CV regions as in FIG. 21. The measurements were made for each of the sections 1 and 2 of FIG. 21, using Image J. As shown under the heading "CV region" in the range evaluation in Table 2, the Cy3 maximum signal intensity for Cyp1a2 was enhanced from 39.75 to 151.00 when the number of oligo DNA probes was increased from 1 to 5. The value is comparable to the maximum signal intensities (137.88 in section 1, and 142.38 in section 2) of Alb in the PV region.

As demonstrated above, by adjusting the number and concentration of the oligo DNA probes used for more than one target gene in the presence of the dummy oligo DNA, substantially the same level of signal intensity can be obtained, even when the expression levels of the target genes differ by a factor of $10^2$ to $10^3$.

TABLE 2

| | | Probe concentration | Number of | IntD. | | | | FLU | Cy3 |
| | | | | PV region | | CV region | | Alb | Cyp1a2 |
| Section ID | Gene | Total (nM) | probes | ave. | s.d. | ave. | s.d. | PV/CV | CV/PV |
|---|---|---|---|---|---|---|---|---|---|
| | | | | Contrast evaluation | | | | | |
| Section 1 | Alb | 1 | 2 | 41.96 | 2.92 | 26.07 | 1.98 | 1.609 | |
| Section 2 | Alb | 1 | 2 | 41.26 | 3.02 | 22.80 | 1.85 | 1.810 | |
| Section 1 | Cyp1a2 | 2 | 1 | 6.88 | 0.40 | 9.79 | 0.56 | | 1.422 |
| Section 2 | Cyp1a2 | 10 | 5 | 11.49 | 0.98 | 26.53 | 2.81 | | 2.309 |
| | | | | Range evaluation | | | | | |
| | | Probe concentration | Number of | Range (signal max-min) | | | | Range ratio | |
| | | | | PV region | | CV region | | Alb | Cyp1a2 |
| Section ID | Gene | Total (nM) | probes | ave. | s.d. | ave. | s.d. | PV/CV | CV/PV |
| Section 1 | Alb | 1 | 2 | 137.88 | 10.99 | 98.38 | 7.87 | 1.402 | |
| Section 2 | Alb | 1 | 2 | 142.38 | 10.62 | 104.38 | 5.13 | 1.364 | |
| Section 1 | Cyp1a2 | 2 | 1 | 33.88 | 7.18 | 39.75 | 5.78 | | 1.173 |
| Section 2 | Cyp1a2 | 10 | 5 | 57.25 | 13.84 | 151.00 | 12.42 | | 2.638 |

EXAMPLE 10

Tyramide Concentration

Figure 22:
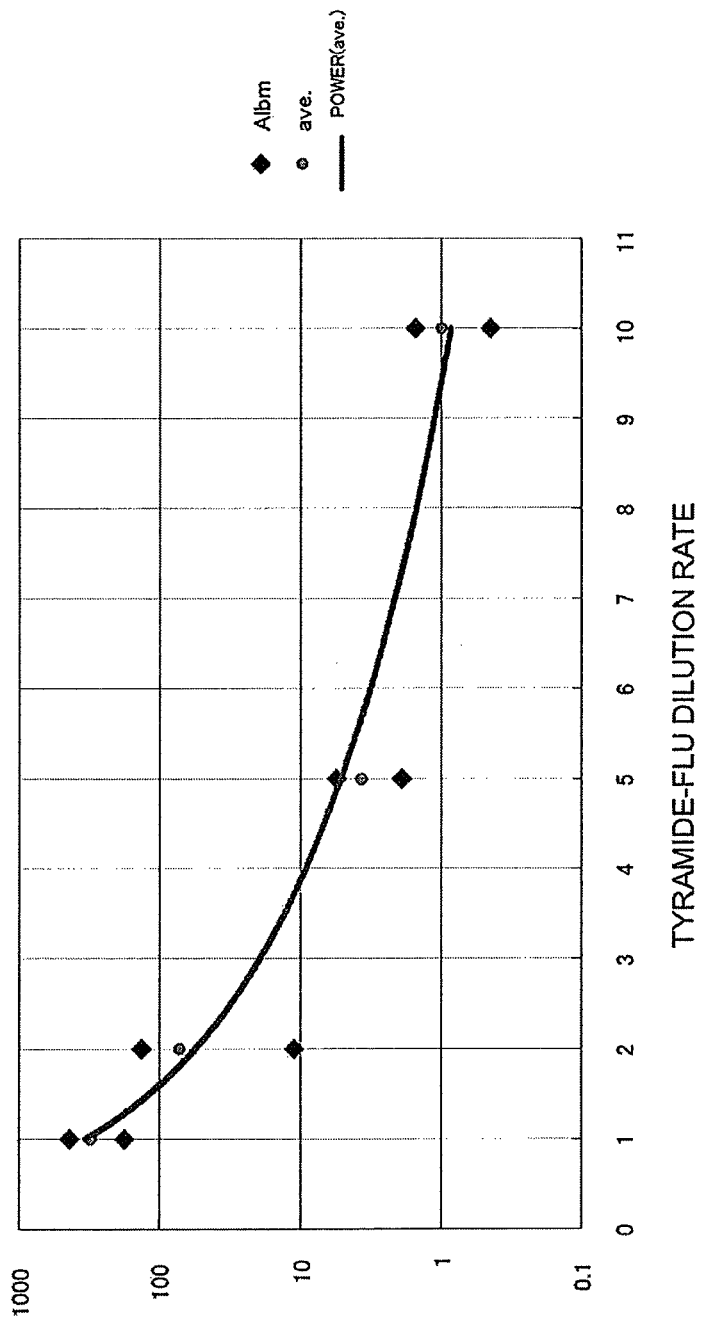
FIG. 22 represents the influence of tyramide-Flu concentration in tyramide sensitivity amplification in Example 10.

The influence of tyramid-FLU (Perkin-Elmer, TSA Plus Fluorescein System, NEL741B001KT) concentration in tyramide sensitivity amplification was examined using an oligo DNA probe (SEQ ID NO: 12; FITC-labeled at the both ends; concentration, 1 nM) for the albumin (Alb) gene in the mouse liver. In the experiment, the mouse liver was prepared into serial sections after usual formalin fixation and paraffin embedding. After treating the specimens with Protease K (Invitrogen, Proteinase K SOL. RNA, 25530049), and RNA in situ hybridization was performed using the oligo DNA probe, and an unlabeled oligo DNA of SEQ ID NO: 29 for the rat Actb gene as the dummy oligo DNA. The dummy oligo DNA was used at a concentration of 8 nM. For the FITC label detection, the anti-FITC rabbit polyclonal antibody P5100 (Dako) was used. The result is shown in FIG. 22. Experiments were performed at the diluted tyramide-FLU concentrations (1×, 2×, 5×, and 10×), according to the protocol recommended by the manufacturer. As shown in FIG. 22, the signal intensity decreases with decrease in tyramide-FLU concentration. Micrographs were taken with a 10× objective lens, using a Zeiss fluorescence microscope Axioplan2 and a CCD camera AxioCam. The resulting images were processed using Image J, and signal intensities were determined.

EXAMPLE 11

Different Gene is also Usable

Figure 23:
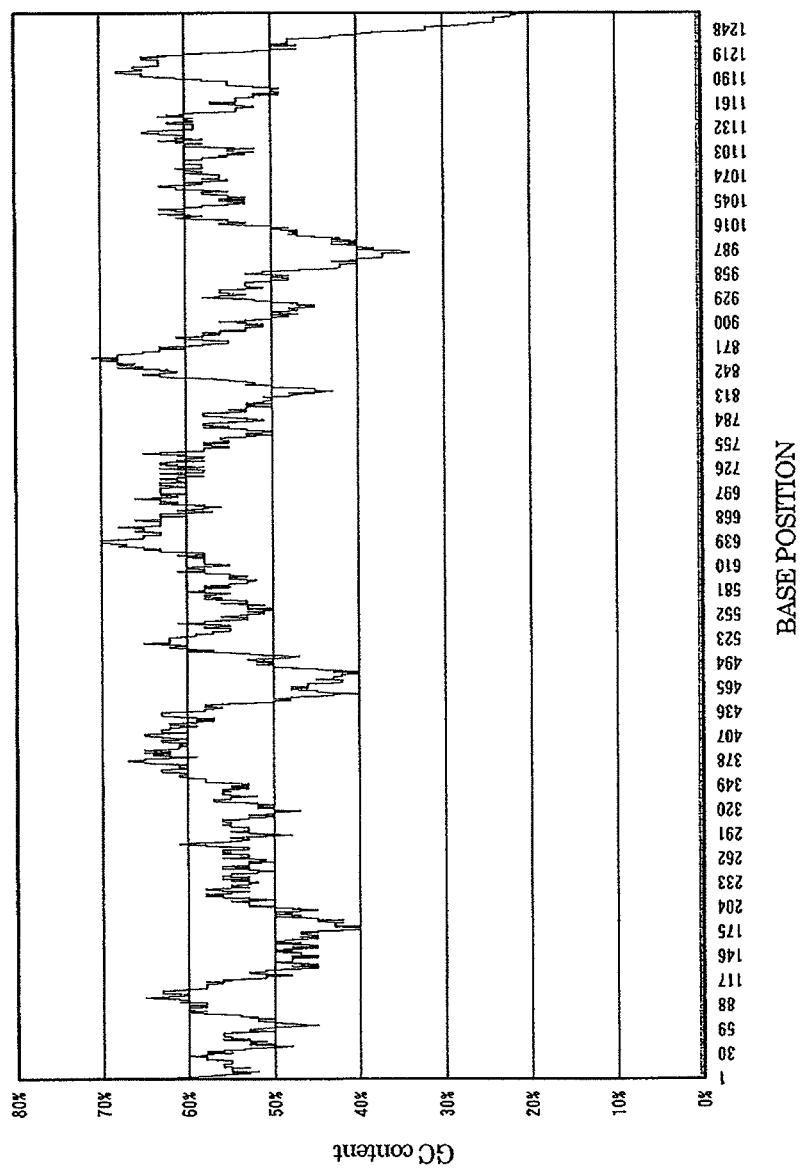
FIG. 23 represents an example of a calculation performed to determine the GC content (%) in each oligonucleic acid in Example 11.

FIG. 23 represents an example of a calculation of the GC content (%) in each oligonucleic acid. The calculation was performed by shifting a window of an oligonucleic acid probe length (40 bases in this example) base by base from the 5' end of a rat GAPDH gene mRNA sequence.

EXAMPLE 12

Using Salmon Sperm DNA

This Example examined how hybridization is influenced by the position and number of the labels added to the oligo- nucleic acid probe, by observing the signal intensity of in situ hybridization for the rat actin beta gene Actb in rat lungs (FIG. 24). Specifically, the rat lungs were prepared into serial sections after usual formalin fixation and paraffin embedding. After deparaffinization and Protease K (Invitrogen, Proteinase K SOL, RNA, 25530049) treatment, RNA in situ hybridization was performed using an oligo DNA probe FITC-labeled at the 5' end (probe 1), an ago DNA probe FITC-labeled at the 3' end (probe 2), and an oligo DNA probe FITC-labeled at the 5' and 3' ends (probe 3), and the resulting fluorescence intensities were compared. In this Example, salmon sperm DNA was used instead of the dummy oligo DNA. The three RTC-labeled oligo DNA probes had the same sequence length, 40 bases, and are represented by SEQ ID NO: 29. In the experiment, FITC was detected using a POD-conjugated, FITC-label detecting anti-FITC antibody protein (Dako, anti-FITC rabbit polyclonal antibody, P5100). TSA sensitization was performed upon addition of tyramide-FLU. A Perkin-Elmer kit (TSA Plus Fluorescein System, NEL741B001KT) was used for TSA sensitization, which was performed according to the protocol attached to the kit. The concentration of the hybridization probe was 5 nM in all samples. Micrographs were taken with a 10× objective lens, using a Zeiss fluorescence microscope Axioplan2 and a CCD camera AxioCam. FIGS. 24a, 24b, and 24c represent the results of rat lung Actb gene mRNA detection with probes 1, 2, and 3, respectively. The Actb gene mRNA signal intensity was about the same for samples detected with the 5'-end labeled probe 1 and for samples detected with the 3'-end labeled probe 2. The Actb gene mRNA signal intensity detected with probe 3 that had the labels at the both ends was about twice as high as those detected with probes 1 and 2. Specifically, the signal intensity is dependent on the number of labels, and the detection sensitivity can be increased by using probes labeled at the both ends. Note that the sequence of the Actb sense probe shown in FIG. 24d is the complementary strand of SEQ ID NO: 29.

EXAMPLE 13

Nonnumerical Signal Intensity with Use of Salmon Sperm DNA

Figure 25:
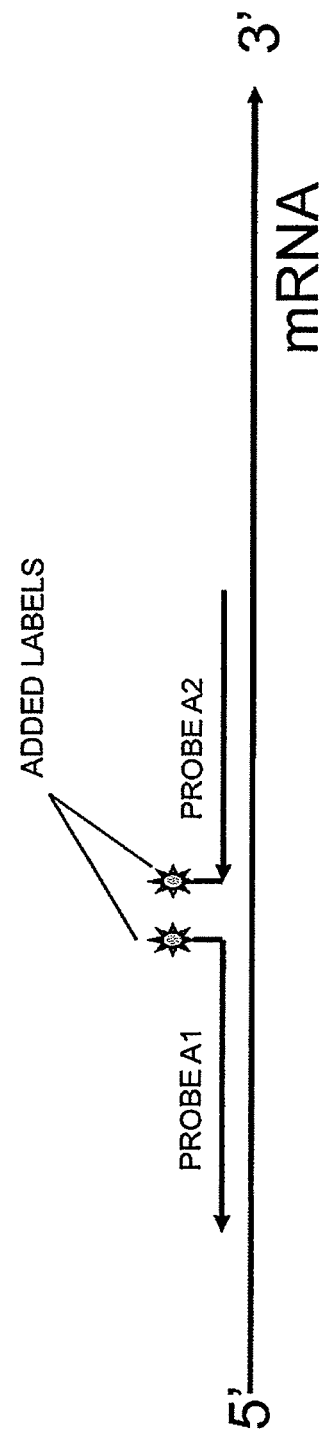
FIG. 25 is a conceptual view of two oligo DNA probes confirming the required distance between two labels on an mRNA nucleic acid sequence in the detection of a hybridized product using more than one label on a single-gene mRNA in Example 13.

Assessment was made as to the required distance between two labels on an mRNA nucleic acid sequence in the detection of a hybridized product that uses more than one label on the mRNA of a single gene. The distance varies depending on the label sensitization method, and the resolution of the optical system including a microscope and a CCD camera. In this Example, two oligonucleic acid probes A1 and A2 were prepared for the nucleic acid sequence of GAPDH gene mRNA, and the 5' end of A1 and the 3' end of A2 were FITC labeled (FIG. 25). The labeled probes A1 and A2 were 40 bases long. Four probes A21, A22, A23, and A24 (SEQ ID NOS: 31, 32, 33, and 34, respectively) were used as A2 so that the 3' end of each probe was separated from the 5' end of A1 (SEQ ID NO: 30) by the distances of 3 bases, 5 bases, 8 bases, and 11 bases, respectively. Rat lungs were used as the sample tissue, which was prepared into serial sections after usual formalin fixation and paraffin embedding. After Protease K (Invitrogen, Proteinase K SOL. RNA, 25530049) treatment, RNA in situ hybridization was performed using the probe sets (A1 and A21, A1 and A22, A1 and A23, and A1 and A24), and the salmon sperm DNA. For the FITC detection, the anti-FITC rabbit polyclonal antibody P5100 (Dako) was used, and TSA sensitization was performed using a Perkin-Elmer kit (TSA Plus Fluorescein System, NEL741B001KT). Micrographs were taken with a 10× objective lens, using a Zeiss fluorescence microscope Axioplan2 and a CCD camera AxioCam. As shown in FIG. 26, signals are additively enhanced when the distance between the 3' end of A1 and the 5' end of A2 is 8 bases or more. In other words, the distance between the labels needs to be at least 8 bases long.

EXAMPLE 14

Nonnumerical Signal Intensity with Use of Salmon Sperm DNA

Four 40-bases-long oligonucleic acid probes FITC-labeled at the both ends and having the GC contents of 40% (SEQ ID NO: 35), 50% (SEQ ID NO: 29), 60% (SEQ ID NO: 36), and 70% (SEQ ID NO: 37) were used for rat ACTS gene mRNA. RNA in situ hybridization was performed in rat lungs with individual probes, and TSA sensitization (Perkin-Elmer, TSA Plus Fluorescein System, NEL741B001KT) was performed using an anti-FITC antibody (Dako, anti-FITC rabbit polyclonal antibody, P5100). Micrographs were taken with a 10× objective lens, using a Zeiss fluorescence microscope Axioplan2 and a CCD camera AxioCam (FIG. 27). It can be seen that signals are enhanced and the detection sensitivity increases as the probe GC content increases. In other words, because the hybridization equilibrium constant K and melting temperature Tm are increasing functions of GC content, the signal intensity and detection sensitivity increase with increase in melting temperature Tm. Note that the sequence of the Actb sense probe in FIG. 27 is the complementary strand of SEQ ID NO: 29.

EXAMPLE 15

Dummy Oligo DNA

The dummy oligo DNAs used in Examples 1 to 10 are SEQ ID NOS: 5 to 11, and SEQ ID NO: 29. SEQ ID NO: 5, and SEQ ID NOS: 7 to 11 were selected from the repeat sequences derived from human genome transposon. SEQ ID NO: 6 was selected from the sequence of the peroxidase gene of the plant *Arabidopsis*. SEQ ID NO: 29 was selected from rat Actb gene, and does not hybridize with the target gene Alb mRNA of Example 10. Further, the oligo DNA synthesized by the sequential A-to-T, T-to-A, G-to-C, and C-to-G substitutions from the 5' side, and by the substitution of the contiguous sequence TTTT with ATAA in the oligo DNA probe of SEQ ID NO: 27: 5'-gtcttggtagtgctcctggacagttttctgcagaaacagc-3' also can be used as the dummy oligo DNA [5'-cagaaccatcac-gaggacctgtcataagacgtctttgtcg-3' (SEQ ID NO: 38)]. In this example, the dummy oligonucleic acid of SEQ ID NO: 38 has the same length and the same GC content as the oligo DNA probe (SEQ ID NO: 27).

The invention claimed is:

1. An RNA in situ hybridization method for identifying a presence of an mRNA of a target gene in a tissue sample consisting of the steps of:
   (i) hybridizing the tissue sample with one or more oligonucleic acid probes labeled with a low-molecular-weight compound on at least one of the bases of the one or more oligonucleic acid probes, which hybridizes to the mRNA of the target gene expressed in the tissue sample and one or more different dummy oligonucleic acids that are substantially equal in length with the one or more oligonucleic acid probes, wherein the one or more different dummy oligonucleic acids neither hybridize with the mRNA of the target gene expressed in the tissue sample nor with the oligonucleic acid probes, and wherein the one or more dummy oligonucleic acids are adsorbed to sites of the tissue sample where the one or more of the oligonucleic acid probes are non-specifically adsorbed and prevent non-specific adsorption of one or more of the oligonucleic acid probes to the tissue sample and
   (ii) detecting the low-molecular-weight compound with an antibody enzyme conjugate that binds to the low-molecular-weight compound and amplifying a signal using a color-developing compound or a fluorescent molecule compound as a substrate for the enzyme, and further detecting the signal by a 10× to 40× objective lens; thereby identifying the presence of the mRNA of the target gene.

2. The RNA in situ hybridization method of claim 1, wherein the amounts of the dummy oligonucleic acids are 2 to 10 times the amounts of the oligonucleic acid probes.

3. The RNA in situ hybridization method of claim 2, wherein the oligonucleic acid probes and the dummy oligonucleic acids are substantially equal in base length within a range of from 20 bp to 70 bp.

4. The RNA in situ hybridization method of claim 1, wherein the low-molecular-weight compound label is added to a 5' end base and/or a 3' end base of the oligonucleic acid probes.

5. The RNA in situ hybridization method of claim 1, wherein two or more of the oligonucleic acid probes are hybridized with the mRNA by being separated from each other by a distance of 8 or more bases between the 5' end of one probe and the 3' end of the other probe, wherein the low-molecular-weight compound label is added to a 5' end base and/or a 3' end base of the oligonucleic acid probes.

6. The RNA in situ hybridization method of claim 1, wherein the tissue sample is a tissue isolated from mammal, and wherein the dummy oligonucleic acids are oligonucleic acids that correspond to partial sequences of retrotransposon repeat sequences.

7. The RNA in situ hybridization method of claim 1, wherein the tissue sample is a tissue isolated from mammal, and wherein the dummy oligonucleic acids are oligonucleic acids that correspond to part of a plant genome, or partial sequences of a microorganism genome.

8. The RNA in situ hybridization method of claim 1, wherein the dummy oligonucleic acids are oligonucleic acids obtained by the A-to-T, T-to-A, G-to-C, and C-to-G substitutions of the base sequences of the oligonucleic acid probes,
   the dummy oligonucleic acids including the substitution of M×0.2 bases (rounded up to the nearest integer) to M×0.8 bases (rounded down to the nearest integer) with the complementary bases in a contiguous sequence of M or more same bases (M=4) when M or more same bases are present, and
   the dummy oligonucleic acids including the substitution of at least N×0.2 bases (rounded up to the nearest integer) with the complementary bases in the presence of a palindromic sequence of N or more bases (N=5) identical to its complementary sequence when read from the 5' side or 3' side, the at least N×0.2 bases being at most (N/2−1) bases when N is an even number, and being at most ((N−1)/2−1) bases when N is an odd number.

9. A set of dummy oligonucleic acids used for the RNA in situ hybridization method of claim 6, wherein the dummy oligonucleic acids are partial sequences of retrotransposon repeat sequences, or different partial sequences of the repeat sequences.

10. A set of dummy oligonucleic acids for the RNA in situ hybridization method of claim 7, wherein the dummy oligonucleic acids are part of a plant genome or partial sequences of a microorganism genome, or different partial sequences of a plant genome or a microorganism genome.

* * * * *

SEQUENCE LISTING

```
<160> NUMBER OF SEQ ID NOS: 38

<210> SEQ ID NO 1
<211> LENGTH: 40
<212> TYPE: DNA
<213> ORGANISM: Artificial sequence
<220> FEATURE:
<223> OTHER INFORMATION: Synthetic construct

<400> SEQUENCE: 1
catccagaac actaaacaga agatggcagt ggccagtagc                              40

<210> SEQ ID NO 2
<211> LENGTH: 40
<212> TYPE: DNA
<213> ORGANISM: Artificial sequence
<220> FEATURE:
<223> OTHER INFORMATION: Synthetic construct

<400> SEQUENCE: 2
gaagaagtcc actgcattcc ctgaggtgac attctccaca                              40

<210> SEQ ID NO 3
<211> LENGTH: 40
<212> TYPE: DNA
<213> ORGANISM: Artificial sequence
```

<220> FEATURE:
<223> OTHER INFORMATION: Synthetic construct

<400> SEQUENCE: 3
tcattgaagg tcttaaacct cttgagggcc gggttgggca        40

<210> SEQ ID NO 4
<211> LENGTH: 40
<212> TYPE: DNA
<213> ORGANISM: Artificial sequence
<220> FEATURE:
<223> OTHER INFORMATION: Synthetic construct

<400> SEQUENCE: 4
cgctgtgctt gaacagggca cttgtgatgt cttggatact        40

<210> SEQ ID NO 5
<211> LENGTH: 40
<212> TYPE: DNA
<213> ORGANISM: Artificial sequence
<220> FEATURE:
<223> OTHER INFORMATION: Synthetic construct

<400> SEQUENCE: 5
tagtcccagc tactcaggaa gctgaggtgg gaggatggct        40

<210> SEQ ID NO 6
<211> LENGTH: 40
<212> TYPE: DNA
<213> ORGANISM: Artificial sequence
<220> FEATURE:
<223> OTHER INFORMATION: Synthetic construct

<400> SEQUENCE: 6
gctcccggcg atacgagggt ccgatcttag ctcgttgaca        40

<210> SEQ ID NO 7
<211> LENGTH: 40
<212> TYPE: DNA
<213> ORGANISM: Artificial sequence
<220> FEATURE:
<223> OTHER INFORMATION: Synthetic construct

<400> SEQUENCE: 7
cttataagtg ggagctgaac aatgagaaca catggacaca        40

<210> SEQ ID NO 8
<211> LENGTH: 40
<212> TYPE: DNA
<213> ORGANISM: Artificial sequence
<220> FEATURE:
<223> OTHER INFORMATION: Synthetic construct

<400> SEQUENCE: 8
gggaggggaa cattgcacac cagggcctgt tgtgggggag        40

<210> SEQ ID NO 9
<211> LENGTH: 40
<212> TYPE: DNA
<213> ORGANISM: Artificial sequence
<220> FEATURE:
<223> OTHER INFORMATION: Synthetic construct

<400> SEQUENCE: 9
agccatcctc ccacctcagc ttcctgagta gctgggacta        40

<210> SEQ ID NO 10
<211> LENGTH: 40
<212> TYPE: DNA
<213> ORGANISM: Artificial sequence
<220> FEATURE:
<223> OTHER INFORMATION: Synthetic construct

<400> SEQUENCE: 10
tgtgtccatg tgttctcatt gttcagctcc cacttataag          40

<210> SEQ ID NO 11
<211> LENGTH: 40
<212> TYPE: DNA
<213> ORGANISM: Artificial sequence
<220> FEATURE:
<223> OTHER INFORMATION: Synthetic construct

<400> SEQUENCE: 11
ctcccccaca acaggccctg gtgtgcaatg ttcccctccc          40

<210> SEQ ID NO 12
<211> LENGTH: 40
<212> TYPE: DNA
<213> ORGANISM: Artificial sequence
<220> FEATURE:
<223> OTHER INFORMATION: Synthetic construct

<400> SEQUENCE: 12
ctggagatac tgggaaaagg caatcaggac taggcctttg          40

<210> SEQ ID NO 13
<211> LENGTH: 40
<212> TYPE: DNA
<213> ORGANISM: Artificial sequence
<220> FEATURE:
<223> OTHER INFORMATION: Synthetic construct

<400> SEQUENCE: 13
cgcagtgtcc gaggaagata gctgttcctt aactttggca          40

<210> SEQ ID NO 14
<211> LENGTH: 40
<212> TYPE: DNA
<213> ORGANISM: Artificial sequence
<220> FEATURE:
<223> OTHER INFORMATION: Synthetic construct

<400> SEQUENCE: 14
caggggttat atccgtttta accggaagtc cagtcttggc          40

<210> SEQ ID NO 15
<211> LENGTH: 27
<212> TYPE: DNA
<213> ORGANISM: Artificial sequence
<220> FEATURE:
<223> OTHER INFORMATION: Synthetic construct

<400> SEQUENCE: 15
gaacagctat cttcctcgga cactgcg          27

<210> SEQ ID NO 16
<211> LENGTH: 27
<212> TYPE: DNA
<213> ORGANISM: Artificial sequence
<220> FEATURE:
<223> OTHER INFORMATION: Synthetic construct

<400> SEQUENCE: 16
ggtagaggcg aagtccttat cttccac                                   27

<210> SEQ ID NO 17
<211> LENGTH: 28
<212> TYPE: DNA
<213> ORGANISM: Artificial sequence
<220> FEATURE:
<223> OTHER INFORMATION: Synthetic construct

<400> SEQUENCE: 17
attgatgcca agactggact tccggtta                                  28

<210> SEQ ID NO 18
<211> LENGTH: 26
<212> TYPE: DNA
<213> ORGANISM: Artificial sequence
<220> FEATURE:
<223> OTHER INFORMATION: Synthetic construct

<400> SEQUENCE: 18
tgtccttcca aatgagctgg caagtg                                    26

<210> SEQ ID NO 19
<211> LENGTH: 30
<212> TYPE: DNA
<213> ORGANISM: Artificial sequence
<220> FEATURE:
<223> OTHER INFORMATION: Synthetic construct

<400> SEQUENCE: 19
ggagtttccc aaacactcag tgaaacaaag                                30

<210> SEQ ID NO 20
<211> LENGTH: 31
<212> TYPE: DNA
<213> ORGANISM: Artificial sequence
<220> FEATURE:
<223> OTHER INFORMATION: Synthetic construct

<400> SEQUENCE: 20
acttcaacaa gaacagtatc caagacatca c                              31

<210> SEQ ID NO 21
<211> LENGTH: 22
<212> TYPE: DNA
<213> ORGANISM: Artificial sequence
<220> FEATURE:
<223> OTHER INFORMATION: Synthetic construct

<400> SEQUENCE: 21
gggtgcatcg ctggtaacat cc                                        22

<210> SEQ ID NO 22
<211> LENGTH: 27
<212> TYPE: DNA
<213> ORGANISM: Artificial sequence
<220> FEATURE:
<223> OTHER INFORMATION: Synthetic construct

<400> SEQUENCE: 22
ctcaagatcg cattcatgcg tcttcac                                   27

<210> SEQ ID NO 23
<211> LENGTH: 28
<212> TYPE: DNA
<213> ORGANISM: Artificial sequence
<220> FEATURE:
<223> OTHER INFORMATION: Synthetic construct

<400> SEQUENCE: 23
aaatcccttc acactctttt tggagata                                          28

<210> SEQ ID NO 24
<211> LENGTH: 40
<212> TYPE: DNA
<213> ORGANISM: Artificial sequence
<220> FEATURE:
<223> OTHER INFORMATION: Synthetic construct

<400> SEQUENCE: 24
aagcacatgg caccaatgac gttagccacc gattccacca                             40

<210> SEQ ID NO 25
<211> LENGTH: 40
<212> TYPE: DNA
<213> ORGANISM: Artificial sequence
<220> FEATURE:
<223> OTHER INFORMATION: Synthetic construct

<400> SEQUENCE: 25
gtcttggtag tgctcctgga cagttttctg cagaaacagc                             40

<210> SEQ ID NO 26
<211> LENGTH: 40
<212> TYPE: DNA
<213> ORGANISM: Artificial sequence
<220> FEATURE:
<223> OTHER INFORMATION: Synthetic construct

<400> SEQUENCE: 26
atgttgacaa tcttctcctc ggggatgaga ccgccattgt                             40

<210> SEQ ID NO 27
<211> LENGTH: 40
<212> TYPE: DNA
<213> ORGANISM: Artificial sequence
<220> FEATURE:
<223> OTHER INFORMATION: Synthetic construct

<400> SEQUENCE: 27
ctcatggatc ttcctctgca cgttaggcca tgtcacaagt                             40

<210> SEQ ID NO 28
<211> LENGTH: 40
<212> TYPE: DNA
<213> ORGANISM: Artificial sequence
<220> FEATURE:
<223> OTHER INFORMATION: Synthetic construct

<400> SEQUENCE: 28
cggcaacaca cgtctttgca aagtctgtta cttcctgcac                             40

<210> SEQ ID NO 29
<211> LENGTH: 40
<212> TYPE: DNA
<213> ORGANISM: Artificial sequence
<220> FEATURE:
<223> OTHER INFORMATION: Synthetic construct

<400> SEQUENCE: 29
ctttaatgtc acgcacgatt tccctctcag ctgtggtggt            40

<210> SEQ ID NO 30
<211> LENGTH: 40
<212> TYPE: DNA
<213> ORGANISM: Artificial sequence
<220> FEATURE:
<223> OTHER INFORMATION: Synthetic construct

<400> SEQUENCE: 30
atttctcgtg gttcacaccc atcacaaaca tgggggcatc            40

<210> SEQ ID NO 31
<211> LENGTH: 40
<212> TYPE: DNA
<213> ORGANISM: Artificial sequence
<220> FEATURE:
<223> OTHER INFORMATION: Synthetic construct

<400> SEQUENCE: 31
gtggtgcagg atgcattgct gacaatcttg agggagttgt            40

<210> SEQ ID NO 32
<211> LENGTH: 40
<212> TYPE: DNA
<213> ORGANISM: Artificial sequence
<220> FEATURE:
<223> OTHER INFORMATION: Synthetic construct

<400> SEQUENCE: 32
tggtggtgca ggatgcattg ctgacaatct tgagggagtt            40

<210> SEQ ID NO 33
<211> LENGTH: 40
<212> TYPE: DNA
<213> ORGANISM: Artificial sequence
<220> FEATURE:
<223> OTHER INFORMATION: Synthetic construct

<400> SEQUENCE: 33
agttggtggt gcaggatgca ttgctgacaa tcttgaggga            40

<210> SEQ ID NO 34
<211> LENGTH: 40
<212> TYPE: DNA
<213> ORGANISM: Artificial sequence
<220> FEATURE:
<223> OTHER INFORMATION: Synthetic construct

<400> SEQUENCE: 34
agcagttggt ggtgcaggat gcattgctga caatcttgag            40

<210> SEQ ID NO 35
<211> LENGTH: 40
<212> TYPE: DNA
<213> ORGANISM: Artificial sequence
<220> FEATURE:
<223> OTHER INFORMATION: Synthetic construct

<400> SEQUENCE: 35
aattgaatgt agtttcatgg atgccacagg attccatacc            40

```
<210> SEQ ID NO 36
<211> LENGTH: 40
<212> TYPE: DNA
<213> ORGANISM: Artificial sequence
<220> FEATURE:
<223> OTHER INFORMATION: Synthetic construct

<400> SEQUENCE: 36
ggatgcggca gtggccatct cttgctcgaa gtctagggca                          40

<210> SEQ ID NO 37
<211> LENGTH: 40
<212> TYPE: DNA
<213> ORGANISM: Artificial sequence
<220> FEATURE:
<223> OTHER INFORMATION: Synthetic construct

<400> SEQUENCE: 37
ctgtcaggtc ccggccagcc aggtccagac gcaggatggc                          40

<210> SEQ ID NO 38
<211> LENGTH: 40
<212> TYPE: DNA
<213> ORGANISM: Artificial sequence
<220> FEATURE:
<223> OTHER INFORMATION: Synthetic construct

<400> SEQUENCE: 38
cagaaccatc acgaggacct gtcataagac gtctttgtcg                          40
```